(12) United States Patent
Röder et al.

(10) Patent No.: US 7,879,620 B2
(45) Date of Patent: *Feb. 1, 2011

(54) METHOD AND SYSTEM FOR DETERMINING WHETHER A DRUG WILL BE EFFECTIVE ON A PATIENT WITH A DISEASE

(75) Inventors: Heinrich Röder, Steamboat Springs, CO (US); Maxim Tsypin, Steamboat Springs, CO (US); Julia Grigorieva, Steamboat Springs, CO (US)

(73) Assignee: Biodesix, Inc., Steamboat Springs, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/661,129

(22) Filed: Mar. 10, 2010

(65) Prior Publication Data

US 2010/0204061 A1 Aug. 12, 2010

Related U.S. Application Data

(63) Continuation of application No. 11/396,328, filed on Mar. 31, 2006, now Pat. No. 7,736,905.

(51) Int. Cl.
*G01N 24/00* (2006.01)
(52) U.S. Cl. .......... 436/173; 436/86; 436/171; 435/6; 435/69.9; 435/372; 702/20; 702/179
(58) Field of Classification Search .......... None
See application file for complete search history.

(56) References Cited

U.S. PATENT DOCUMENTS 4,802,102 A 1/1989 Lacey .......... 702/32

(Continued)

FOREIGN PATENT DOCUMENTS

WO WO 00/22649 4/2000

(Continued)

OTHER PUBLICATIONS

Dyer et al., "Enhancement of Raman Spectra Obtained at Low Signal-to-Noise Ratios: Matched Filtering and Adaptive Peak Detection", Applied Spectroscopy, vol. 39, No. 4, pp. 655-662 (1985).

(Continued)

*Primary Examiner*—Yelena G Gakh
*Assistant Examiner*—Robert Xu
(74) *Attorney, Agent, or Firm*—McDonnell Boehnen Hulbert & Berghoff LLP

(57) ABSTRACT

A process of determining whether a patient with a disease or disorder will be responsive to a drug, used to treat the disease or disorder, including obtaining a test spectrum produced by a mass spectrometer from a serum produced from the patient. The test spectrum may be processed to determine a relation to a group of class labeled spectra produced from respective serum from other patients having the or similar clinical stage same disease or disorder and known to have responded or not responded to the drug. Based on the relation of the test spectrum to the group of class labeled spectra, a determination may be made as to whether the patient will be responsive to the drug.

8 Claims, 11 Drawing Sheets

U.S. PATENT DOCUMENTS

| | | | |
|---|---|---|---|
| 5,291,426 | A | 3/1994 | Collins et al. ............... 702/195 |
| 5,538,897 | A | 7/1996 | Yates, III et al. ............. 436/89 |
| 5,592,653 | A | 1/1997 | Guedan et al. ................ 710/62 |
| 5,672,869 | A | 9/1997 | Windig et al. ............... 250/282 |
| 6,017,693 | A | 1/2000 | Yates, III et al. ............... 435/5 |
| 6,366,870 | B2 | 4/2002 | Jarman et al. ............... 702/179 |
| 6,675,104 | B2 | 1/2004 | Paulse et al. ................. 702/22 |
| 6,675,106 | B1 | 1/2004 | Keenan et al. ............... 702/28 |
| 6,696,040 | B2 | 2/2004 | Driehuys .................... 424/9.3 |
| 6,829,539 | B2 | 12/2004 | Goodlett et al. .............. 702/20 |
| 6,849,121 | B1 | 2/2005 | Iseler et al. .................... 117/81 |
| 6,906,320 | B2 | 6/2005 | Sachs et al. ................ 250/282 |
| 6,925,389 | B2 | 8/2005 | Hitt et al. ...................... 702/19 |
| 7,016,884 | B2 | 3/2006 | Platt et al. ..................... 706/20 |
| 7,027,933 | B2 | 4/2006 | Paulse et al. ................. 702/27 |
| 7,096,206 | B2 | 8/2006 | Hitt ............................. 706/12 |
| 7,112,408 | B2 | 9/2006 | Ye et al. ...................... 435/7.1 |
| 7,113,896 | B2 | 9/2006 | Zhang et al. .................. 703/2 |
| 7,240,038 | B2 | 7/2007 | Hitt ............................. 706/12 |
| 7,314,717 | B2 | 1/2008 | Jackowski et al. ........... 435/7.1 |
| 2002/0115056 | A1 | 8/2002 | Goodlett ........................ 435/4 |
| 2002/0119490 | A1 | 8/2002 | Aebersold et al. ........... 435/7.1 |
| 2003/0068825 | A1 | 4/2003 | Washburn et al. ............. 436/86 |
| 2004/0102906 | A1 | 5/2004 | Röder ......................... 702/22 |
| 2005/0048547 | A1 | 3/2005 | Zhao et al. ..................... 435/6 |
| 2005/0164218 | A1 | 7/2005 | Agus et al. ..................... 435/6 |
| 2005/0209786 | A1 | 9/2005 | Chen et al. .................... 702/20 |
| 2005/0260671 | A1 | 11/2005 | Hitt et al. ....................... 435/6 |
| 2005/0267689 | A1 | 12/2005 | Tsypin ........................ 702/19 |
| 2006/0029574 | A1 | 2/2006 | Albitar et al. .............. 424/93.1 |
| 2006/0064253 | A1 | 3/2006 | Hitt et al. ...................... 702/22 |
| 2007/0185824 | A1 | 8/2007 | Hitt ............................. 706/25 |

FOREIGN PATENT DOCUMENTS

| | | |
|---|---|---|
| WO | WO2003/006951 | 1/2003 |
| WO | WO 03/017177 | 2/2003 |
| WO | WO 03/075306 | 9/2003 |
| WO | WO 2004/012588 | 2/2004 |
| WO | WO 2005/010492 | 2/2005 |
| WO | WO 2005/098445 | 10/2005 |

OTHER PUBLICATIONS

Jarman et al., "A New Approach to automated Peak Detection", Chemometrics and Intelligent Laboratory Systems, vol. 69, pp. 61-76 (2003).

Rouh et al., "Bayesian Signal Extraction from Noisy FT NMR Spectra", Journal of Biomolecular NMR vol. 4, pp. 505-518 (1994).

Koradi et al., "Automated Peak Picking and Peak Integration in Macromolecular NMR Spectra Using AUTOPSY", Journal of Magnetic Resonance, vol. 135, pp. 288-297 (1998).

Breen et al., "Automatic Poisson Peak Harvesting for High Throughput Protein Identification", Electrophoresis, vol. 21, pp. 2243-2251 (2000).

Li et al., "Parametric Deconvolution of Positive Spike Trains", Ann. Statistics, vol. 28, No. 5, pp. 1279-1301 (2000).

Kato et al, "New Deconvolution Method for ElectroSpray Ionization Mass Spectrometry", J. Mass. Spectrom. Soc. Jpn., vol. 48, No. 6, pp. 373-379 (2000).

Raznikov et al., "A New Approach to Data Reduction and Evaluation in High-resolution Time-of-flight Mass Spectrometry using a Time-to-digital Convertor Data-recording System", Rapid Communications in Mass Spectrometry, vol. 15, pp. 570-578 (2001).

Fleming et al. "Windowed mass selection method: a new data processing algorithm for liquid chromatography-mass spectrometry data", Journal of Chromatography A, vol. 849, pp. 71-85 (1999).

Mann et al., "Error-tolerant identification of peptides in sequence databases by peptide sequence tags", Anal. Chem. vol. 66, pp. 4390-4399 (1994).

Dancik et al. "De novo peptide sequencing via tandem mass spectrometry", Journal of Computational Biology, vol. 6, Nos. 3/4, pp. 327-342 (1999).

Keller et al., "Experimental protein mixture for validating tandem mass spectral analysis", OMICS: J. Integrative Biology, vol. 6, No. 2, pp. 207-212 (2002).

Pappin et al., "Chemistry, mass spectrometry and peptide-mass databases: Evolution of methods for the rapid identification and mapping of cellular proteins",Mass Spectrometry in the Biological Sciences, Burlingame et al. eds. Humana Press, Totowa, NJ, pp. 135-150 (1996).

James et al. "Protein identification in DNA databases by peptide mass fingerprinting", Protein Science, vol. 3, pp. 1347-1350 (1994).

Pappin et al., "Rapid identification of proteins by peptide-mass fingerprinting", Current Biology, vol. 3, No. 6, pp. 327-332 (1993).

Bleasby et al. "Construction of validates, non-redundant composite protein sequence databases", Protein Engineering, vol. 3, No. 3, pp. 153-159 (1990).

Yates, "Database searching using mass spectrometry data", Electrophoresis, vol. 19, pp. 893-900 (1998).

Stetson, "DAOPHOT:A Computer program for crowded-field stellar photometry", Publications of the Astronomical Society of the Pacific, vol. 99, pp. 191-222 (1987).

Bertin et al., "SExtractor: Software for source extraction", Astronomy & Astrophysics, Supplement Series, vol. 117, pp. 393-404 (1996).

Gras et al., "Improving protein identification from peptide mass fingerprinting through a parameterized multi-level scoring algorithm and an optimized peak detection", Electrophoresis, vol. 20, pp. 3535-3550 (1999).

Horn et al., "Automated reduction and interpretation of high resolution electrospray mass spectra of large molecules from resolved isotopic distributions", J. American Society for Mass Spectrometry, vol. 6, pp. 229-233 (2000).

Carroll et al., "Using matrix convolution filters to extract information from time-of-flight mass spectra", Rapid Communications Mass Spectrometry vol. 10, pp. 1683-1687 (1996).

Senko et al., "Determination of monoisotopic masses and ion population for large biomolecules from resolved isotopic distribution", Journal of the American Society for Mass Spectrometry, vol. 6, pp. 229-233 (1995).

IBM, "Mascot protein identification solution from IBM and Matrix Science", at http://www.03.ibm.com/industries/healthcare/us/detail/solution/Y297020U01362X74.html.

Tabb, "GutenTag: Software for automated sequence tag identification of peptides", The Scripps Research Institute, at http://fields.scripps.edu/GutenTag (copyright 2003).

Eng et al., "SEQUEST", http://en.wikipedia.org/wiki/SEQUEST, Apr. 2, 2009.

Eng et al., "An approach to correlate tandem mass spectral data of peptides with amino acid sequences in a protein database", Journal of the American Society of Mass Spectrometry, vol. 5, pp. 976-989 (1994).

Colinge et al., "High-performance peptide identification by tandem mass spectrometry allows reliable automatic data processing in proteomics", Proteomics, vol. 4, pp. 1977-1984 (2004).

Colinge et al., "OLAV: towards high-throughput tandem mass spectrometry data identification", Proteomics, vol. 3, pp. 1454-1463 (2003).

Magnin et al., "OLAV-PMF: a novel scoring scheme for high-throughput peptide mass fingerprinting", Journal of Proteome Research, vol. 3, pp. 55-60 (2004).

Havillo et al, "Intensity-based statistical scorer for tandem mass spectrometry", Analytical Chemistry, vol. 75, No. 3, pp. 435-444 (2003).

Várhegyi et al., "Computer processing of thermogravimetric-mass spectrometric and high pressure thermogravimetric data. Part I: smoothing and differentiation", Thermochimica Acta, vol. 329, pp. 141-145 (1999).

Definition of "sum", Webster's Ninth New Collegiate Dictionary, Merriam-Webster Inc., Springfield, Massachusetts, p. 1181 (1991).

Srinivasan et al., "Activation of Abl Tyrosine Kinases Promotes Invasion of Aggressive Breast Cancer Cells" Cancer Research vol. 66, No. 11, pp. 5648-5655 (2006).
Office Action dated Jul. 22, 2008 in U.S. Appl. No. 10/887,138.
Office Action dated Feb. 4, 2009 in U.S. Appl. No. 10/887,138.
Amendment to Accompany Request for Continued Examination filed Oct. 22, 2008 in U.S. Appl. No. 10/887,138.
Duin et al. "Classifier Conditional Posterior Probabilities", Advances in Pattern Recognition, Joint IAPR Int. Workshops SSPR '98 and SPR '98, Sydney, Australia. Lecture Notes in Computer Science, vol. 1451/1998, ISBN 978-3-540-64858-1, pp. 611-619, Springer, Berlin (1998).
Lynch et al., *Activating Mutations in the Epidermal Growth Factor Receptor Underlying Responsiveness of Non-Small-Cell Lung Cancer to Gefitnib*, New England Journal of Medicine, vol. 350(21), pp. 2129-2139 (2004).
Alfassi, *On the Normalization of a Mass Spectrum for Comparison of Two Spectrum*, American Society for Mass Spectrometry, vol. 15, pp. 385-387 (2004).
Mazet et al., *Background removal from spectra by designing and minimizing a non-quasratic cost function*, Chemometrics and Intelligent Laboratory Systems, vol. 76, pp. 121-131 (2005).
U.S. Appl. No. 12/321,394, filed Jan. 20, 2009.
U.S. Appl. No. 12/321,393, filed Jan. 20, 2009.
U.S. Appl. No. 12/321,392, filed Jan. 20, 2009.
Written Opinion of International Searching Authority in PCT/US2007/007467 dated Nov. 8, 2007.
Extended European Search Report dated Aug. 25, 2010 in European Application No. 10003343.0.
Bhanot et al. *A robust meta-classification strategy for cancer detection from MS data* Proteomics, vol. 6, NR 2, pp. 592-607 (Jan. 2006).
Reyzer et al. *MALDI mass spectrometry for direct tissue analysis: a new tool for biomarker discovery*, Journal of Proteome Research vol. 4, No. 4, pp. 1138-1142 (2005).
Yanagisawa et al. *Proteomic patterns of tumour subsets in non-small-cell lung cancer*, The Lancet, vol. 362, pp. 433-439 (Aug. 9, 2003).
D. Coomans and D.L. Massart, "Alternative $k$-Nearest Neighbour Rules in Supervised Pattern Recognition", Part 1, Analytica Chimica Acta, 136, pp. 15-27 (1982).
Office Action in EP application No. 07754043.3 dated Sep. 14, 2010.
Howard et al. *Identification and validation of a potential lung cancer serum biomarker detected by matrix-assisted laser desorption/ionization-time of flight spectra analysis*, Proteomics vol. 3, pp. 1720-1724 (2003).

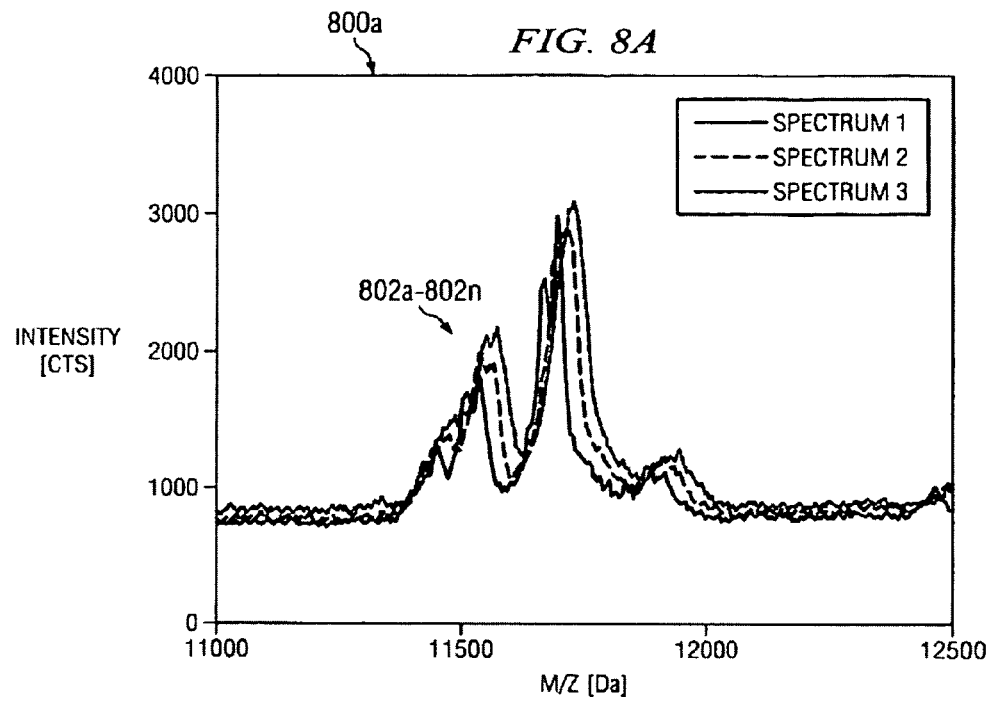
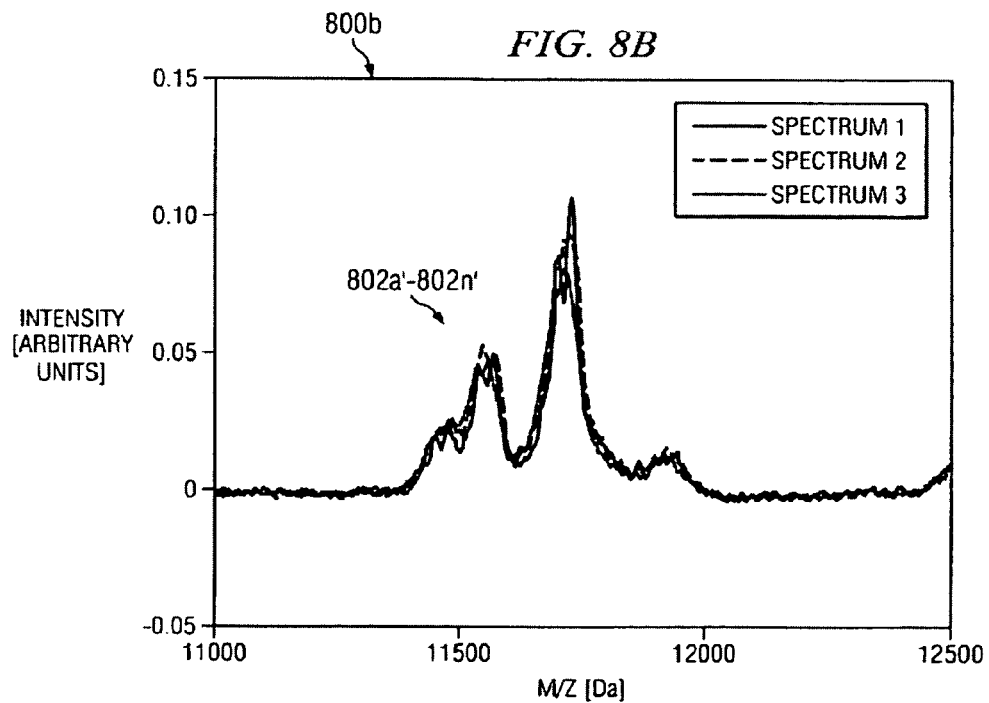

METHOD AND SYSTEM FOR DETERMINING WHETHER A DRUG WILL BE EFFECTIVE ON A PATIENT WITH A DISEASE

CROSS-REFERENCE TO RELATED APPLICATION

This continuation of U.S. patent application Ser. No. 11/396,328 filed Mar. 31, 2006, now U.S. Pat. No. 7,736,905.

BACKGROUND

The inventors of the instant invention have found a novel method of determining if a patient will respond to a treatment by testing the patient's biomarkers by mass spectroscopy. As an example of one embodiment of this invention, the inventors have applied their technique to a cancer, Non-Small-Cell Lung Cancer (NSCLC).

Non-Small-Cell Lung Cancer is a leading cause of death from cancer in both men and women in the United States. There are at least four (4) distinct types of NSCLC, including adenocarcinoma, squamous cell, large cell, and bronchoaldeolar carcinoma. Squamous cell (epidermoid) carcinoma of the lung is a microscopic type of cancer most frequently related to smoking. Adenocarcinoma of the lung accounts for over 50% of all lung cancer cases in the U.S. This cancer is more common in women and is still the most frequent type seen in non-smokers. Large cell carcinoma, especially those with neuroendocrine features, is commonly associated with spread of tumors to the brain. When NSCLC enters the blood stream, it can spread to distant sites such as the liver, bones, brain, and other places in the lung.

Treatment of NSCLC has been relatively poor over the years. Chemotherapy, the mainstay treatment of advanced cancers, is only marginally effective, with the exception of localized cancers. While surgery is the most potentially curative therapeutic option for NSCLC, it is not always possible depending on the stage of the cancer.

Recent approaches for developing anti-cancer drugs to treat the NSCLC patient focus on reducing or eliminating the ability for cancer cells to grow and divide. These anti-cancer drugs are used to disrupt the signals to the cells to tell them whether to grow or die. Normally, cell growth is tightly controlled by the signals that the cells receive. In cancer, however, this signaling goes wrong and the cells continue to grow and divide in an uncontrollable fashion, thereby forming a tumor. One of these signaling pathways begins when a chemical in the body, called epidermal growth factor, binds to a receptor that is find on the surface of many cells in the body. The receptor, known as the epidermal growth factor receptor (EGFR) sends signals to the cells, through the activation of an enzyme called tyrosine kinase (TK) that is found within the cells. The signals are use to notify cells to grow and divide.

Two anti-cancer drugs that were developed and prescribed to the NSCLC patients are called gefitinib (trade name "Iressa") and erlotinib (trade name "Tarceva"). These anti-cancer drugs target the EGFR pathway and have shown promise in being effective toward treating NSCLC cancer. Iressa inhibits the enzyme tyrosine kinase that is present in lung cancer cells, as well as other cancers in normal tissues, and that appears to be important to the growth of cancer cells. Iressa has been used as a single agent of the treatment of NSCLC that has progressed after, or failed to respond to, two other types of chemotherapies.

However, response rates have only been between 10% and 20% in Caucasian populations, and have led the Federal Drug Administration (FDA) in 1995 to withdraw support for the application of Iressa as a second-line treatment. Surprisingly, the response rate in Asia has been considerably higher and Iressa is stilled used. Traceva is still approved and routinely given to patients, but still has response rate concerns. While it appears that Iressa and Traceva have the ability to be effective in some patients, they may not be generic drugs effective in treating all patients. There may be many factors involved in a patient's ability to respond to these drugs that are currently unknown. However, if a determination of factors that could be used to predict the effectiveness of a NSCLC patient to respond to these anti-cancer drugs, the FDA could allow these anti-cancer drugs to be prescribed to those patients having conditions that indicate that they would be responsive to these drugs. Doctors could then prescribe these drugs to those patients predicted to respond to the anti-cancer drugs with the knowledge that their patients would be responsive to the treatments.

SUMMARY

To overcome the problem of the low rates of treatment success using drugs, the principles of the present invention provide for a diagnostic test to determine whether a patient will respond to these drug treatments. The determination is made by detecting differentiating peaks of a spectrum produced by a mass spectrometer from serum extracted from a patient's blood. Biomarkers are measurable and quantifiable biological parameters that can be evaluated as an indicator of normal or abnormal biologic processes or pathogenic processes. The mass spectrometer produces a spectrum having certain peaks that that can be utilized to compare with spectra produced from serum of patients that were responsive and non-responsive to the drug treatments. It is often not necessary to actually determine what chemical compound is located in the peak. The spectrum itself is a valuable fingerprint that can characterize the treatment potential for the drug in a specific patient. Some embodiments of the present invention encompass isolating the material that is in the peaks and determining what materials are elevated or diminished in the sample.

More specifically, the principles of the present invention are directed to a process of determining whether a patient with a disease or disorder will be responsive to a drug or treatment used to treat the disease or disorder. The process includes obtaining a test spectrum produced by a mass spectrometer from a serum of a patient. The test spectrum may be processed to determine a relation to a group of class labeled spectra produced from respective serum from other patients at the same or similar clinical stage disease or disorder and known to have responded or not responded to the drug. Based on the relation of the test spectrum to the group of class labeled spectra, a determination may be made as to whether the patient will be responsive to the drug or treatment. In processing the test spectrum, background reduction, normalization and alignment of the test spectrum may be performed to better match the test spectrum with the group of class labeled spectra, which have been processed in the same or similar manner. By processing raw spectra to generate the class labeled spectra, the determination of whether the drug will be effective can be made independent of the particular clinics and mass spectrometers used to process the serum of the patient.

Other embodiments in accordance with the principles of the present invention include systems for determining whether a patient will be responsive to a drug or treatment. The systems may include a storage device configured to store a test spectrum produce by a mass spectrometer from a serum produce from a patient with a disease or disorder and a group of class labeled spectra produced from respective serum from other patients at the same or similar clinical stage disease or disorder and known to have responded or not responded to a drug or treatment. Such systems may further include a processor in communication with a storage device, where the processor executes software to (i) obtain a test spectrum produce by a mass spectrometer from a serum produced from a patient having a disease or disorder, (ii) process the test spectrum to determine a relation to a group of class labeled spectra produced from respective serum from other patients having the same or similar clinical stage disease or disorder and known to have responded or not responded to a drug or treatment, (iii) determine, based on the relation of the test spectrum to the group of class labeled spectra, whether the patient will be responsive to the drug. In one embodiment, the system is in communication with a network, such as the Internet, for communication with laboratories and clinics that communicate test spectra for testing. The determination of the relation of the test spectra to the group of class labeled spectra may include outputting an indicator or class label representative of potential responsiveness of the patient to the drug or treatment. The indicator may be a positive, negative, or inconclusive so that a medical professional may determine whether or not to prescribe the drug or treatment. In some embodiments, the disease or disorder is cancer. In other embodiments, the cancer type is non-small-cell lung cancer. In yet another embodiment, the system may be utilized to determine whether the drug gefitinib and/or erlotinib will be effective in treating non-small-cell lung cancer patients.

BRIEF DESCRIPTION OF THE DRAWINGS

FIGS. 8A and 8B are graphs showing multiple sample spectra being aligned;

DETAILED DESCRIPTION OF THE DRAWINGS

Figure 1:
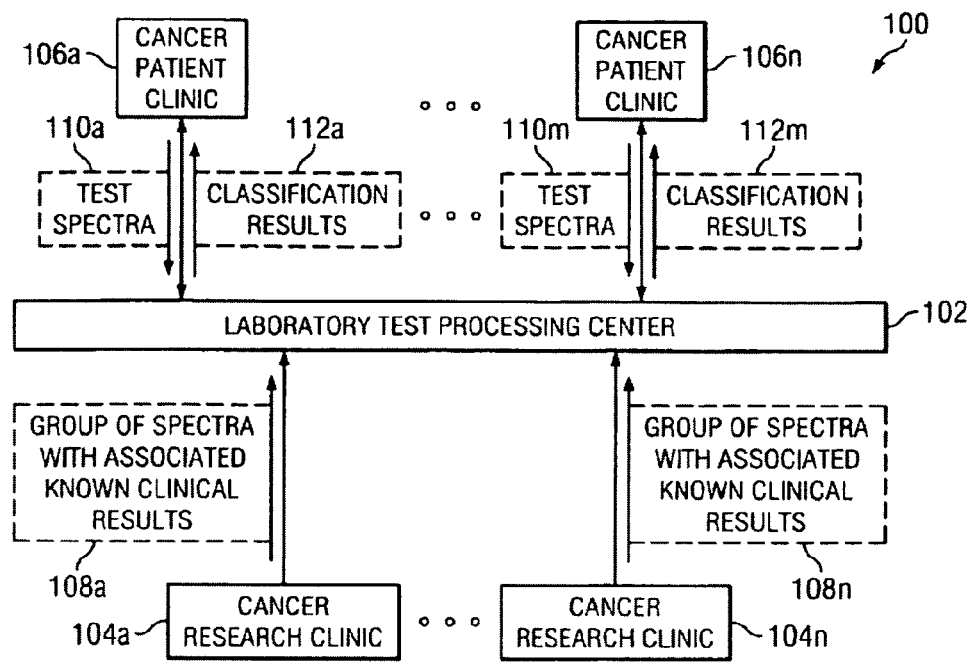
FIG. 1 is a block diagram of an exemplary relationship between a laboratory test processing center, cancer research clinics, and cancer patient clinics.

FIG. 1 is a block diagram of an exemplary relationship between a laboratory test processing center 102, cancer research clinics 104a-104n (collectively 104), and cancer patient clinics 106a-106m (collectively 106). The laboratory test processing center 102 operates to process tests from cancer research clinics 104 and cancer patient clinics 106. In one embodiment, the cancer research clinics 104 and cancer patient clinics 106 are part of the same organization, such as a hospital. The cancer research clinics 104 perform drug trials and testing to determine effectiveness of certain drugs to treat patients. For example, patients with non-small-cell lung cancer who have gone through clinical studies and tests of various anti-cancer drugs to control growth and spreading of the cancer cells have different responses to the anti-cancer drugs. These anti-cancer drugs may include gefitinib and erlotinib that target the epidermal growth factor receptor pathway. During clinical studies and non-clinical studies, the cancer research clinics 104 carefully monitor various aspects of the treatments, including cancer stages, blood components, cancer progression, patient overall health, and other factors indicative of the patient to determine the effectiveness of the anti-cancer drug.

The cancer research clinics 106 may be any facility that performs clinical studies or otherwise administers cancer medications to cancer patients and monitors effectiveness of the medications. The cancer research clinics 104 may take blood samples and process them to produce serum, which is blood plasma (the liquid component of blood in which blood cells are suspended) having clotting factors, such as fibrin, removed. The serum may be processed and used to produce a spectrum by a mass spectrometer so that biomarkers within the serum can be detected. In one embodiment, the mass spectrometer is a time-of-flight (TOF) mass spectrometer that uses matrix-assisted laser desorption/ionization (MALDI). The spectrum may include surrogate markers or peaks within the spectrum (see FIG. 11) indicative of certain chemicals or matter within the serum.

As a result of the mass spectrometer production of spectra of patients, effectiveness of the anti-cancer drugs being administered to the cancer patient to produce clinical results may be recorded and observed. The laboratory test processing center 102 may use the recorded (quantitative) and observed (general health) results of the patients in determining classifications for each of the cancer patients as to whether each is responsive to the anti-cancer drug(s).

Continuing with FIG. 1, as a result of the mass spectrometer production of spectra of patients, effectiveness of the anti-cancer drugs being administered to the cancer patient to produce clinical results may be recorded and observed. The laboratory test processing center 102 receives the raw spectra with associated known clinical results 108 from the cancer research clinics and performs a classification on each spectrum. The classification of each spectrum, described in detail hereinafter, classifies each spectrum associated with a cancer patient receiving anti-cancer drugs as being responsive, non-responsive, or partially responsive. The classification of the spectra enables the laboratory test processing center 102 to receive test spectra 110a-110m (collectively 110) from cancer patient clinics 106 and perform analysis on these test spectra 110 to determine which classification each test spectrum (i.e., each patient) is most likely to resemble. Alternatively, rather than receiving raw spectra, the laboratory test processing center 102 may receive blood samples or serum samples to process and produce the raw spectra for processing and classification.

In classifying the raw spectra, a decision is made as to whether each spectrum is "good" or "bad" based on whether the cancer patient had a positive response, no response, or limited response to the anti-cancer drug. By comparing the test spectrum from cancer patients with the class labeled spectra, a determination can be made as to the likelihood of a cancer patient from which a test spectrum is generated will have a positive response to the anti-cancer drug. A more detailed description of the comparison process is provided hereinafter. Once the laboratory test processing center 102 has classified the test spectrum 110, and optionally makes the determination as to whether the cancer patient will have a positive response to the anti-cancer drug, classification results 112a-112m (collectively 112) may be delivered to the respective cancer patient clinic 108a, for example. In one embodiment, the classification results are class labels produced by a classifier function as further described herein below.

Although shown separate, the laboratory test processing center 102 may be part of the cancer research clinics 104 or cancer patient clinics 106. In one embodiment, the laboratory test processing center 102 is functionally incorporated into test equipment, such as a mass spectrometer or processing system operating in conjunction with the test equipment. Alternatively, the functionality may be incorporated onto a computer system or other processing system that is configured to perform the various processing utilized in processing and classifying the spectra and not part of or associated with the test equipment. For example, the computer system may be a server operated by the laboratory test processing center 102, clinic research clinic 104, and/or cancer patient clinic 106.

Although FIG. 1 describes cancer clinics, it should be understood that these clinics may be common clinics or clinics specific to a particular disease or illness. Accordingly, the laboratory test processing center 102 is configured to receive and test the particular disease or illness being sent in accordance with the principles of the present invention.

Figure 2:
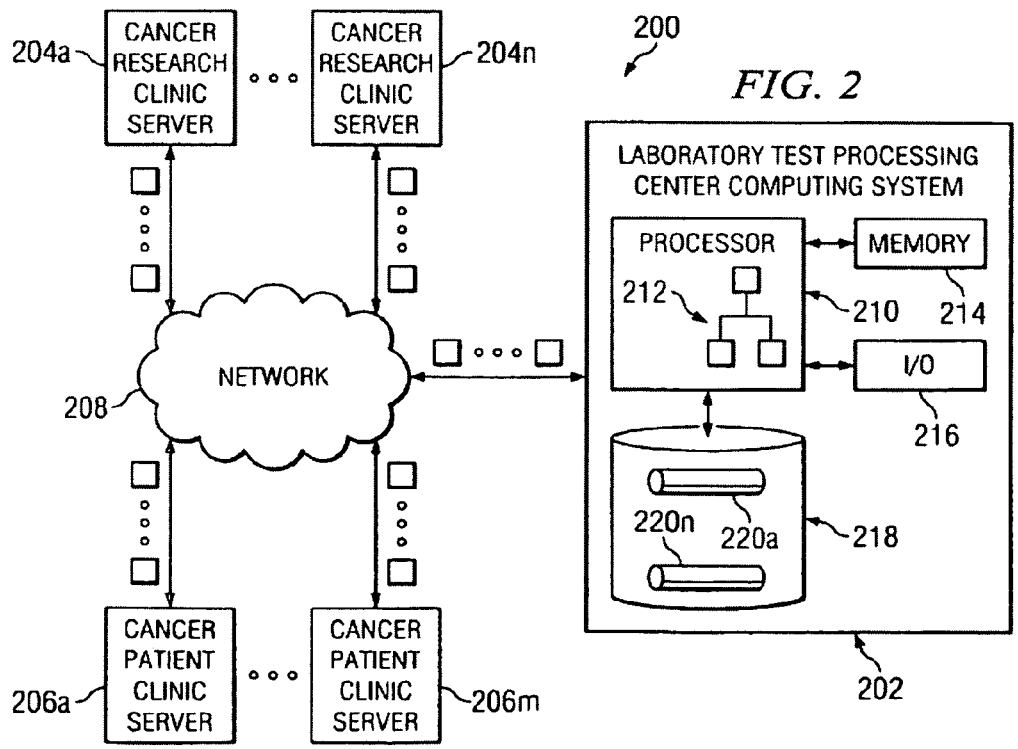
FIG. 2 is a block diagram of an exemplary system for communicating and processing information between the laboratory test processing center, cancer research clinics, and cancer patient clinics of FIG. 1.

FIG. 2 is a block diagram of an exemplary system 200 for communicating and processing information between the laboratory test processing center 102, cancer research clinics 104, and cancer patient clinics 106 of FIG. 1. A laboratory test processing center computing system 202 may be operated by the laboratory test processing center 104. Cancer research clinic servers 204a-204n (collectively 204) may be operated by the cancer research clinics 104 and cancer patient clinic servers 206a-206m (collectively 206) may be operated by the cancer patient clinics 106. Each of the computing system 202 and servers 204 and 206 may communicate over network 208 via digital data packets 209a-209b or other communication technique as understood in the art. The network 208 may be the Internet or other public or non-public communication network.

The laboratory test processing center computing system 202 may include a processor 210 executing software 212 for processing the raw spectra and test spectra to determine classifications of all or a portion thereof in accordance with the principles of the present invention as described further hereinbelow. The computing system 202 may further include memory 214, in which the software 212 may reside when being executed, input/output (I/O) unit 216, which may perform the communication over the network 208, and storage device 218 to which the processor 210 communicates. The storage device 218 may include one or more databases 220a-220n (collectively 220) in which the raw spectra, test spectra, and other related data is stored to enable the laboratory test processing center 102 to determine whether a cancer patient will be responsive to an anti-cancer drug. It should be understood that the storage device 218 may include one or more storage devices and located within or external from the computing system 202. It should further be understood that the processor 210 may include one or more processors. Still yet, it should be understood that the computing system 202 may be directly or indirectly in communication with the network 208.

In accordance with FIG. 1, the cancer research clinic servers 204 may communicate raw spectra with associated known clinical results based on clinical trials of anti-cancer drug to the laboratory test processing center computing system 202. The processor 210, automatically or semi-automatically with the assistance with a scientist or otherwise, may perform classification processing to classify each raw spectrum to classify the raw spectra to form a group of classified spectra. Similarly, the cancer patient clinic servers 206 may communicate test spectra 110 to the laboratory for the processor 210 to automatically or semi-automatically classify the test spectra 110 for the cancer patient clinics 108. The laboratory test processing center computing system 202 may process the test spectra 110 and communicate classification results 112 (FIG. 1) back to the cancer patient clinic servers 206. As a result of classifying the raw spectra and test spectra 112, the computing system 202 may store classification results and utilize the results to generate statistical information that may be used for various other purposes, such as success and failure rates of the anti-cancer drug.

Data analysis plays a central role in the discovery of detecting peaks differentiating spectra from patients with different clinical outcome and their use either as discovery leads for immuno-histochemical assays or directly in mass spectrometry based diagnosis. In developing testing and analysis procedures in accordance with the principles of the present invention, an integrated analysis system containing algorithms designed for comparative analysis of mass spectra has been developed. The integrated analysis system includes a number of tools that facilitates the detection of differentiating peaks in the spectra from mass spectra, while at the same time providing rigorous tools for the assessment of their significance and validation of the results.

Figure 3:
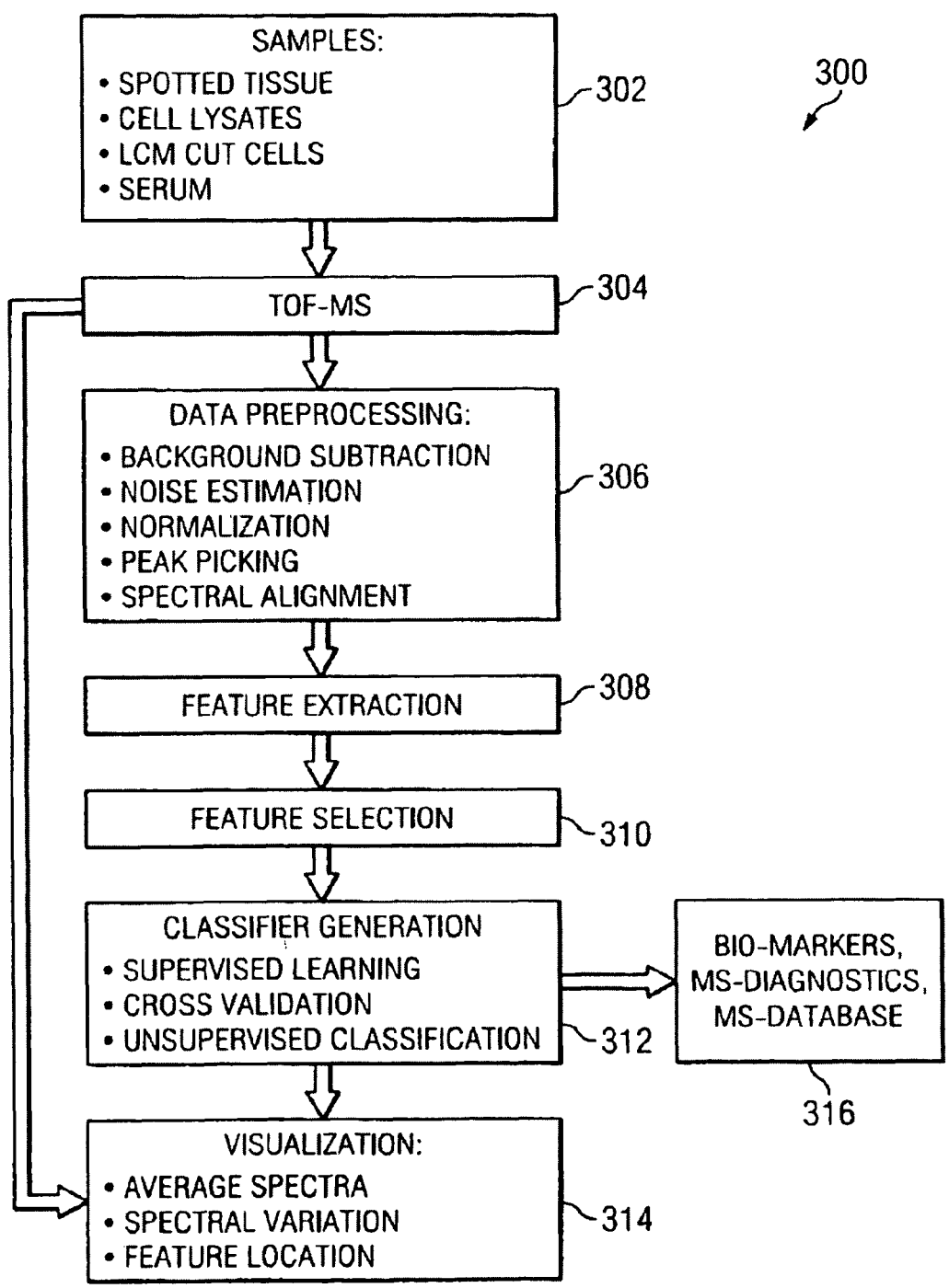
FIG. 3 is a flow diagram of an exemplary workflow process for developing a test for determining whether a cancer patient will be responsive to an anti-cancer drug in accordance with the principles of the present invention.

FIG. 3 is a flow diagram of an exemplary workflow process 300 for developing and performing a test for determining whether a cancer patient will be responsive to an anti-cancer drug in accordance with the principles of the present invention. The process starts at step 302 where samples are taken from cancer patients. Depending on the type of cancer or other disease, spotted tissue, cell lysates, or cut cells may be utilized as samples for generating spectra via a mass spectrometer 304. The mass spectrometer may be an ABI Voyager, an ABI 4700, a Bruker Autoflex or a Bruker Ultraflex mass spectrometer. Other mass spectrometers may similarly be utilized. In the case of non-small-cell lung cancer, serum may be used for generating spectra. By using serum, lung cancer patients in advanced stages of lung cancer, where it is difficult or impossible to take a tissue sample of the patients, may be diagnosed without an invasive procedure. Additionally, bodily liquids, such as urine, may be utilized for samples in detecting peaks in a mass spectrum to determine whether certain anti-cancer drugs will be effective in treating a cancer patient with non-small-cell lung cancer. By utilizing non-invasive procedures to collect serum or other fluids, the cost for diagnosis is significantly lower than if a tissue sample from a lung were needed.

Generating and processing serum used for a test study may include using crude serum samples from individual hospitals. In one embodiment, the crude serum samples may be thawed on ice and centrifuged at 1500 rpm for five minutes at four degrees Celsius. Further, the serum samples may be diluted 1:10, as performed at the University of Colorado Health Sciences Center (UCHSC) or 1:5, as performed at Vanderbilt University medical Center (VUMC), in MilliQ water. Diluted samples may be spotted in randomly allocated positions on a MALDI plate in triplicate (i.e., on three different MALDI targets). After 0.75 ul of diluted serum is spotted on a MALDI plate, 0.75 ul of 35 mg/ml sinapinic acid (in 505 acetonitrile and 0.1% TFA) may be added and mixed by pipetting up and down five times. Plates may be allowed to dry at room temperature. It should be understood that other techniques and procedures may be utilized for preparing and processing serum in accordance with the principles of the present invention.

Mass spectra may be acquired for positive ions in linear mode using a Voyager DE-PRO (UCHSC) or DE-STR (VUMC) with automated or manual collection of the spectra. In one study, 75 (UCHSC) or 100 (VUMC) spectra were collected from seven (UCHSC) or five (VUMC) positions within each MALDI spot in order to generate an average of 525 (UCHSC) or 500 (VUMC) spectra for each serum specimen. Spectra were externally calibrated using a mixture of protein standards (Insulin (bovine), thioredoxin (*E. coli*), and Apomyglobin (equine)). For validation purposes, three replicates of the same sample were run for all specimen resulting in a total of 717 spectra (239 specimen times 3) submitted for analysis for the instant study.

In performing the data analysis, it is generally accepted that cancerous cells have different expression level of specific proteins that are different from normal cells. Distinct stages of disease are accompanied by changes in specific proteins, e.g., changes in the expression level of cell-binding proteins in the case of metastatic cancer. In the case of serum samples, and to delineate serum testing from tissue sample testing, it is unlikely that direct tumor excretions are measured due to dilution of these excretions in the blood. The differentiating peaks in serum (or other bodily liquids) samples arise in all likelihood due to a host response reaction dependent on the disease state, such as autoimmune reactions. As such, it is to be expected that tests based on tissue samples are highly specific, but not necessarily very significant, and serum based mass spectrometer tests should be highly significant, but not so specific. This is born out by the results presented hereinbelow. By detecting differentiating peaks in the spectra, correlation of changes with clinically relevant questions may be performed. To generate differentiating peaks in the spectra of value, independent of their further use, either directly as a diagnostic tool or as leads for immuno-histochemical based testing, the following issues may be addressed during the differentiating peaks discovery process, including the data analysis stage:

Reproducibility: the results of an analysis are to be reproducible. Biomarkers may be identified through differentiating peaks that can be repeatably found in the various diseased and control groups, and the values assigned to these differentiating peaks cannot vary too much within a group. As a simplified measure of reproducibility, coefficients of variations (CV), which have become a standard for assessing diagnostic tests, may be provided by software executed on a processor. The variations of markers within a group, and even within the same sample, may be measured, characterized, and used in downstream analysis and classification.

Robustness: differentiating peaks are to be robust against unavoidable variations in sample preparation and handling, as well as against variations arising from trends in mass spectrometer characteristics. Another reason for patient to patient variability arises from irrelevant differences in the biological state of a patient, for example, the digestive state at the time of sample gathering. Criteria may be developed for distinguishing irrelevant changes from biologically significant ones. In the design of classifiers (i.e., classifier functions or algorithms), which are functions that map from multi-dimensional feature space (e.g., 12 differentiating peaks) to class label space (e.g., "good," "bad," or "undefined") and during feature extraction, real differentiating peaks should not change very much while making small changes to data analysis parameters. Similarly located differentiating peaks should be found in different data sets.

Interpretability: The resulting differentiating peaks may be put in the context of biological interpretability. First, identified differentiating peaks are generally visually noticeable in the mass spectra. The m/z positions of differentiating peaks give valuable information on the biological relevance of underlying biomarkers that cause these differentiating peaks. This allows for the interpretation and filtering of the differentiating peaks arising from biologically irrelevant procedures. For example, the measurement of different hemoglobin content of cancerous versus normal samples, which is purely an artifact of sample preparation. In some cases, it may turn out that clinically relevant differentiating peaks of the spectrum are of non-linear combinations of multiple features in the spectrum, and are not simple up/down regulations. Even in this case, the differentiating peaks that constitute features in the spectra should be visible (FIG. 4), and the functions with which to evaluate markers should be made explicit.

Sensitivity: Great effort is usually undertaken to gather samples and generate mass spectra. Great care is also taken to avoid missing relevant differentiating peaks in the mass spectrometer spectra by using data analysis algorithms that are not selective or sensitive enough to actually find these differentiating peaks in a spectrum. For example, if an m/z range is defined as being relevant to a feature, this range is to be large enough to contain the feature, and should not lump in other features present in the spectrum. Range picking algorithms derive their parameters from the data themselves, optionally in a local manner, and may not depend on external smoothing and pinning parameters.

The task of comparing mass spectra for the extraction of differentiating peaks is made difficult by the specific nature of these spectra due to intrinsic intensity variations. The ionization probability of individual ions depends on the local sample chemistry (e.g., ion suppression effects), and although the mass resolution of modern mass spectrometers is mostly sufficient, the absolute mass scale can vary from spectrum to spectrum.

In accordance with the principles of the present invention, mass spectrometer specific variations may be measured to reduce or eliminate these variations (in the case of background variations) or provide measures to assess the relevant significance of signals by estimating the local noise level. Avoidance of introducing additional variations arising from data preprocessing and analysis may be accomplished. For example, peak picking software that is often bundled with many mass spectrometers has been found to be unreliable to directly use these peaks in a comparative spectral analysis. Early attempts at spectral comparison have instead resorted to using the whole mass spectra itself in their comparison and classification algorithms. Whole spectra, however, includes many thousands of individual data points, most of which are measurements of instrument noise with only relevant information being confined to the peaks in the mass spectra. Further, the interpretation of features in the spectra is complicated and sometimes non-linear in the case of neural network based classification algorithms, and becomes very cumbersome. As a result, the application of these attempts to classify serum samples has led to exaggerated claims that could not be reproduced in other laboratories.

Figure 4:
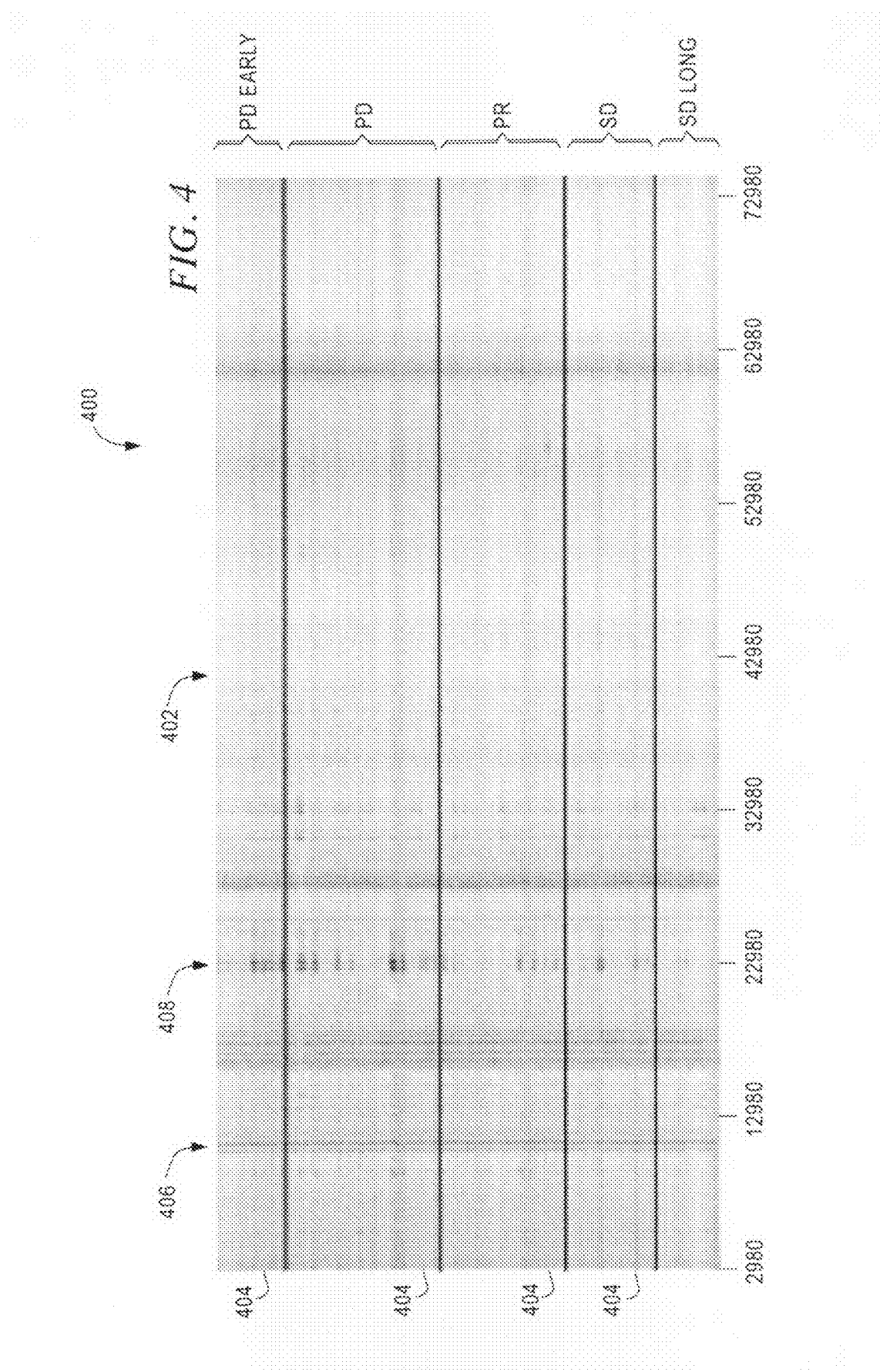
FIG. 4 is an image of an exemplary gel-plot of all spectra used in a test development.

FIG. 4 is an image of an exemplary gel-plot 404 of a markers output by a spectrometer. The spectra is clinically labeled using standard progression labels of the World Health Organization (WHO), including stable disease (SD), progressive disease (PD), and partial responders (PR). However, fine clinical labels, which separate the main clinical labels into extreme clinical labels, are created to include three additional labels of SD-short, SD-long, and PD-early. A gel-plot is a plot where each line corresponds to one mass spectrum of a clinical sample, the horizontal axis is the mass/charge axis, and the grey-scale is depicting the intensity. The clinical labels 402 are provided on the gel-plot 404 with horizontal lines 404 delineating the different clinical labels. The gel-plot 404 is that of all spectra (i.e., spectra received from a cancer research clinic of a control group of non-small-cell lung cancer patients in Italy and Japan who received Iressa as a cancer treatment) used for training a classifier algorithm. Differentiating peaks can be visually seen on each of the spectra at 406 and 408, but are quantitatively measured for accuracy and other quantitative purposes.

In avoiding some of these measurement problems, raw mass spectra may be pre-processed to remove and measure irrelevant artifacts of the mass spectrometry process, and to register them on a similar m/z and amplitude scale.

Continuing with FIG. 3, the process at step 306 performs data preprocessing. The preprocessing may include any or all of background subtraction, noise estimation, normalization, peak picking, and spectral alignment. These processes are illustrated in FIGS. 5-10 and described hereinbelow.

Figure 5:
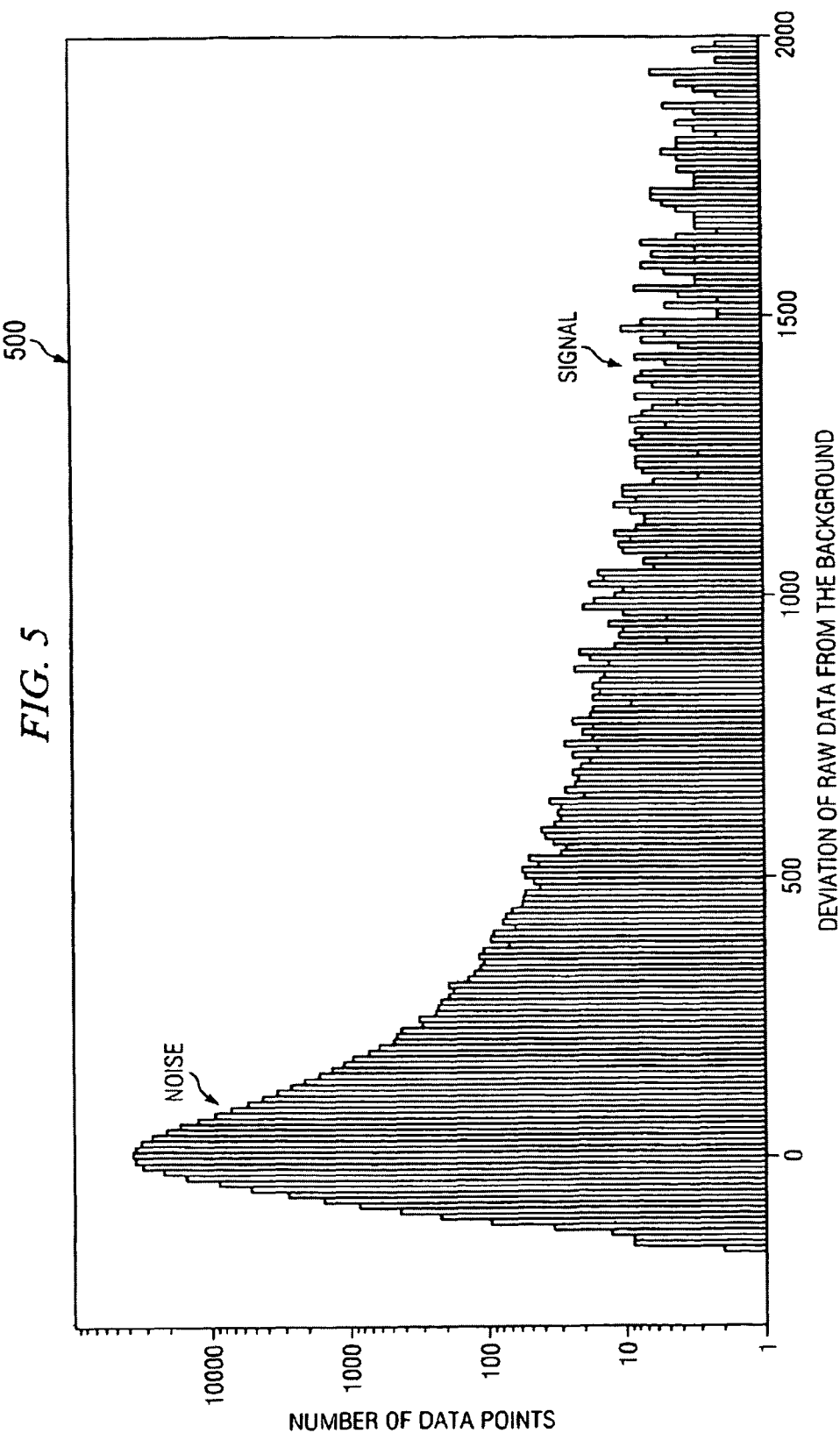
FIG. 5 is a histogram showing an exemplary set of data points output from a spectrometer having noise and signal components.

FIG. 5 is a histogram 500 showing an exemplary set of data points output from a spectrometer having noise and signal components. Background or baseline is a slowly varying component of a mass spectrum—the gradual overall shift of the data across the m/z range. As functional definitions: background is smooth variations of the signal strength that can arise from charge accumulation effects or nonlinear detector characteristics or partial ion decay, etc., as opposed to noise that arises from electronics, random ions, and fluctuates rapidly (in m/z).

Background can be modeled, and, hence, subtracted. Noise is a statistical fluctuation and only its strength can be measured. Further, background can be caused by unresolved "garbage" ions and may be estimated and subtracted before further data processing steps, such as peak detection, can be meaningfully performed. The background may be estimated using robust, local statistical estimators. Obtaining a reliable estimate for the strength of the noise in the data is utilized for subsequent peak detection based on signal-to-noise (S/N) ratio criterion. Such estimators are also used in any spectral comparison tasks to provide a measure of errors. As in the background estimation, asymmetric robust estimators may be utilized to perform this task.

The background is shown to include the most number of data points and the signal includes fewer data points. The background may be determined by iterating using correlation analysis and optimal separation. As background does not contain biologically relevant information and varies from spectrum to spectrum, amplitude information may be made more comparable by subtracting the value of the background from each spectrum. This process is described in co-pending patent application Ser. No. 10/887,138 filed on Jul. 7, 2004, which is incorporated herein in its entirety.

Figure 6A:
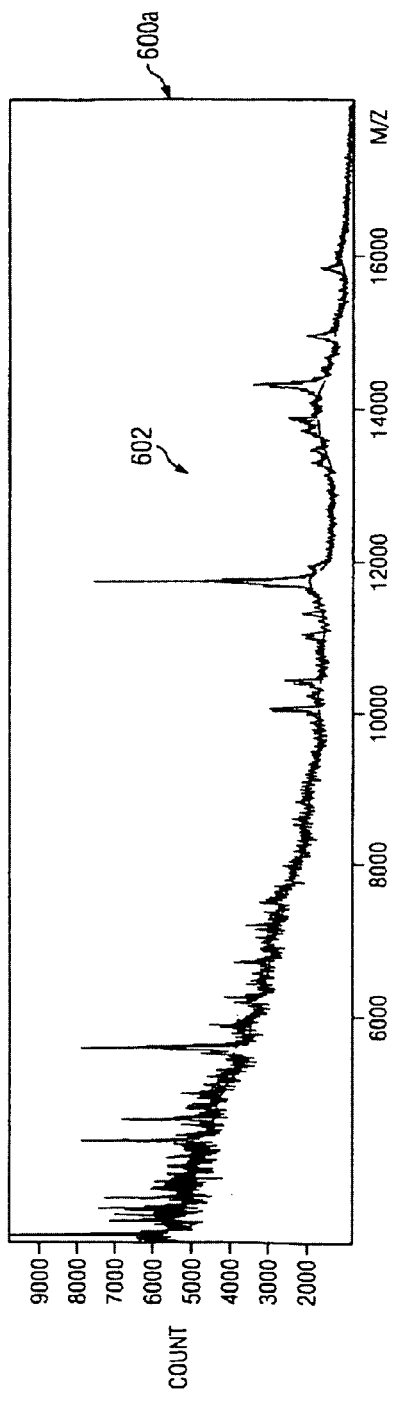
FIGS. 6A and 6B are graphs showing a spectrum with background and without background after the background has been subtracted out of the spectrum, respectively.
Figure 6B:
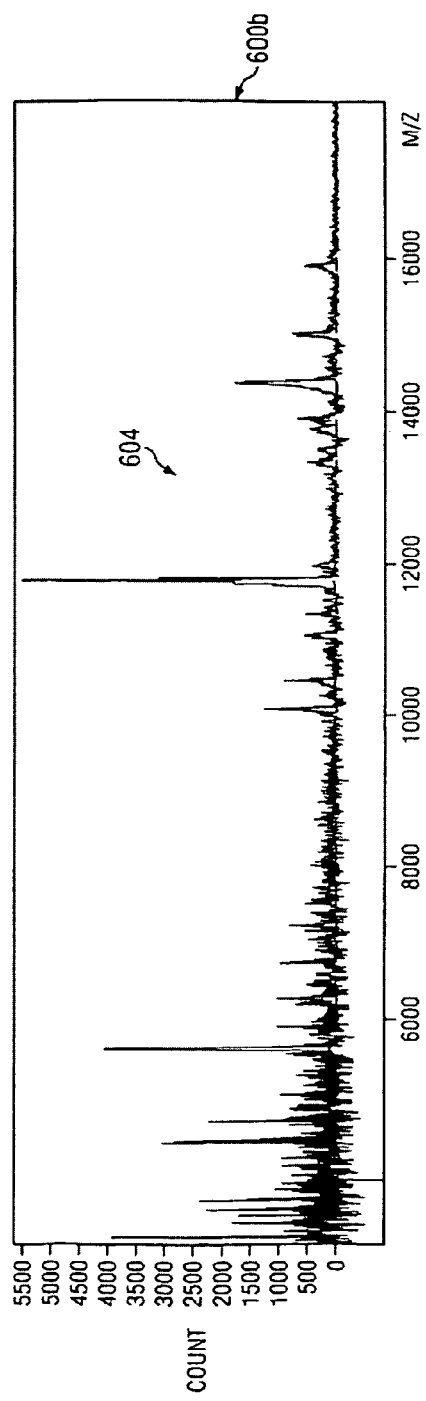

FIGS. 6A and 6B are graphs 600a and 600b showing a spectrum, with background 602 and without background after the background has been subtracted out of the spectrum 604, respectively. As usual in serum, there, are peaks that are highly variable due to natural fluctuations in the abundance of serum proteome. Further, the amount of sample ionized can fluctuate from spectrum to spectrum due to changes in laser power, variations in the amount of ionizable sample, and variations in the positioning of the laser on the MALDI plate. This fluctuation renders standard normalization routines, such as total ion current normalization (i.e., normalization across the entire spectrum), less useful as the fluctuations in these peaks are propagated to the peaks of interest. A partial normalization (i.e., normalization over the spectra that identifies and excludes these variable peaks and regions) may be utilized to avoid results that fluctuate, thereby providing reproducible results.

More particularly, partial ion current normalization may be derived as follows. Mass spectrum includes data points, pairs (m/z, amplitude), arranged in ascending order in m/z. As the spectrum is obtained on a time-of-flight instrument, the m/z axis may be considered segmented into bins. Each data point represents the corresponding bin and its amplitude represents (is proportional to) the ion count in the bin (i.e., ion current in the bin).

The sum of all amplitudes in the spectrum is thus the "total ion current" (TIC). It corresponds to the total number of ions arriving at a detector of the mass spectrometer. Normalization to the total ion current means that for each spectrum, a normalization factor is chosen such that the corresponding normalized spectra (m/z=original m/z, amplitude=(norm factor) *(original amplitude)) have the same (prescribed) total ion current, such as 100.

In general, the total ion current normalization only makes sense after background subtraction. Otherwise, the total ion current is dominated by the integrated background, rather than by ion current in the meaningful signals, such as peaks. In other words, total ion current integrates all available ions and is dominated by large peaks. In the case where the peaks are highly variable, the total ion current is highly variable as well, thereby causing normalization variation, which can lead to false positive detection of differentiating features.

In accordance with the principles of the present invention, detection of "features"—intervals of m/z axis that appear to be "not empty", i.e. not "pure background" due to containing some signal, such as peaks. A feature is a peak that is visible in more than a user-defined number of spectra of a control group of patients. Having a set of features (a collection of non-overlapping m/z intervals) provides for defining a more flexible normalization method, "normalization to partial ion current (PIC)." Partial ion current is the sum of amplitudes in the spectrum for all data points that belong to the specified set of features (typically, a subset of the full set of features). Normalization to the partial ion current means that for each spectrum, a normalization factor may be chosen such that the corresponding normalized spectra (m/z=original m/z, amplitude=(norm factor)*(original amplitude)) have the same (prescribed) partial ion current. In general, partial ion current uses stable peaks for normalization, as the highly variable ones are not included in the calculations. By using stable peaks, stability in the normalization process results.

Peaks from spectra within a control group of patients are included in a list, and a divisive clustering algorithm, as understood in the art, may be used to find clusters of peaks.

TABLE I

Features from PIC Normalization

| ID | m/z center |
|---|---|
| 0 | 3085.867 |
| 1 | 3102.439 |
| 2 | 3107.451 |
| 3 | 3129.212 |
| 4 | 4154.918 |
| 5 | 4187.865 |
| 6 | 4711.48 |
| 7 | 5104.862 |
| 10 | 6433.973 |
| 11 | 6588.426 |
| 12 | 6591.603 |
| 13 | 6632.237 |
| 14 | 6839.537 |
| 15 | 6883.021 |
| 16 | 6941.514 |
| 17 | 7390.573 |
| 20 | 7673.52 |
| 22 | 8206.572 |
| 23 | 8230.679 |
| 24 | 8697.822 |
| 27 | 8822.777 |
| 28 | 8880.021 |
| 29 | 8920.239 |
| 30 | 8940.18 |
| 31 | 9135.182 |
| 32 | 9138.189 |
| 33 | 9157.859 |
| 34 | 9371.936 |
| 35 | 9424.089 |
| 36 | 9432.518 |
| 37 | 9446.061 |
| 38 | 9635.796 |
| 39 | 9638.7 |
| 40 | 9659.863 |
| 41 | 9717.098 |
| 42 | 9738.03 |
| 43 | 9941.016 |
| 44 | 10220.11 |
| 45 | 10504.31 |
| 46 | 10841.693 |
| 53 | 12579.848 |
| 54 | 12771.505 |
| 55 | 12861.925 |
| 56 | 12868.575 |
| 57 | 13082.443 |
| 58 | 13765.804 |
| 59 | 13885.668 |
| 60 | 14050.987 |
| 61 | 14157.312 |
| 62 | 14651.73 |
| 68 | 16206.683 |
| 69 | 17143.885 |
| 70 | 17168.815 |

TABLE I-continued

Features from PIC Normalization

| ID | m/z center |
|---|---|
| 71 | 17272.049 |
| 72 | 17391.032 |
| 73 | 17412.315 |
| 74 | 17590.691 |
| 75 | 17620.442 |
| 76 | 18629.158 |
| 77 | 18824.353 |
| 78 | 19104.212 |
| 79 | 19460.971 |
| 80 | 20868.776 |
| 81 | 21040.264 |
| 82 | 21063.912 |
| 83 | 21275.194 |
| 84 | 22690.405 |
| 85 | 22844.388 |
| 86 | 22927.864 |
| 88 | 23215.972 |
| 89 | 23354.353 |
| 90 | 23451.251 |
| 91 | 24917.423 |
| 92 | 25147.019 |
| 93 | 25185.861 |
| 94 | 25466.131 |
| 95 | 25582.933 |
| 96 | 25813.574 |
| 97 | 28102.608 |
| 98 | 28535.715 |
| 99 | 28889.368 |
| 100 | 28896.086 |
| 101 | 28902.778 |
| 102 | 33277.541 |
| 103 | 33340.741 |
| 104 | 33839.223 |
| 105 | 38830.258 |
| 106 | 43474.948 |
| 107 | 50722.939 |
| 108 | 56307.899 |
| 109 | 57257.535 |
| 110 | 59321.131 |
| 111 | 65392.98 |
| 112 | 66702.45 |
| 113 | 67633.769 |
| 114 | 68328.628 |
| 115 | 73363.308 |
| 116 | 77948.338 |
| 117 | 91016.846 |
| 118 | 96444.862 |
| 119 | 98722.464 |

TABLE I includes a list of the 80% (PIC=0.8) of all features (remaining feature set) that were retained in a PIC normalization. The m/z values are in Daltons with an uncertainty of 1000 ppm (after alignment.

One extreme case of partial ion current normalization is when the full set of features is used to compute the partial ion current. This case is analogous to total ion current normalization, the difference being that the "empty" regions of the spectrum contribute to total ion current, but not to the partial ion current. Thus, contribution of noise in the "empty" region is not included in the partial ion current. Another extreme case is when just one feature is used to compute the partial ion current. If this is the feature containing the strongest peak, base peak normalization is determined.

In spectrum comparison, the reasoning behind the use of partial ion current normalization is as follows. Consider two groups of spectra, such as disease and control. The spectra contain in the order of 100 signals (peaks), and most of the signals are expected to be unchanged between groups, while some signals can be up or down-regulated. In mass spectra, the unnormalized intensities are not directly comparable between spectra. When using total ion current normalization, an assumption is made that up or down-regulated signals are few and weak, so that they do not significantly distort the total ion current, which assumingly dominates the signals that are unchanged between groups. However, in reality, this is not necessarily the case. If, for example, the up-regulated signal is strong enough to significantly contribute to the total ion current, other signals in the normalized data appear to be down-regulated, even if they are actually unchanged. Analogously, if the spectra contain strong and strongly varying signals, other signals in the normalized spectrum show increased coefficients of variation, even if they are inherently stable. Using the partial ion current normalization instead of total ion current, and using the subset of features that contains the most stable features, while omitting up-regulated, down-regulated or highly variable features, can remedy the problem of increased coefficients of variation. The main question is how to select this subset.

To select the subset for partial ion current, the following procedure may be used. If several groups of spectra are obtained, for the purposes of this procedure, the groups of spectra may be combined into one combined set.

First, the subset of features equals a full list of features. Next, the following procedure may be iterated a number of times to produce the new subset of "least variable" features containing one feature less than the original one.

The process may be continued as follows:
Using the original subset of features, normalize all feature values (full set) to the partial ion current.
For each feature, compute the coefficient of variation=(std deviation)/(mean value)
Sort the features according to the absolute value of CV
Select the new subset of features from this sorted list—those with the smallest abs(CV); include one feature less than in the original subset
Replace original subset by the new subset
The termination criteria are the following. The user specifies two values:
the lowest allowed fraction of the ion current
the lowest allowed fraction of the number of features The process is terminated when any of the criteria is broken. Thus, if the user specifies both values (i.e., the lowest allowed fraction of the ion current and number of features) as 0.8, the resulting subset of features is guaranteed to contain at least 80% of the ion current (as computed from the full set of features), as well as at least 80% of the features. Specifying 1.0 for any of the values results in the full feature set being used. Typically 0.8 is about the right value to use for optimal results. Depending on the application, however, higher or lower values may be used. Feature values normalized to the partial ion current can then be used for classification and other purposes.

In summary, partial ion current may be determined as follows:
calculate CVs
drop the peak with the largest CV
stop when the maximal CV is smaller than a specified level
Implementation of the partial ion current may be calculated using two operations. The first operation computes a list of features for use in the PIC .denominator. This operation marker first merges the two selected groups feature values into one two-dimensional array, where rows are spectra (i.e., samples) and columns are feature values corresponding in order to the feature list sorted by CenterMZ. This operation takes in two parameters in addition to the merged feature values. These two parameters are MinAllowedFracOfIC and MinAllowedFracOfFeatures. MinAllowedFracOfIC—minimum allowed fraction of the ion current in the retained subset of features. Keeping these features corresponds to the value of 1. MinAllowedFracOfFeatures—minimum allowed fraction of features in the retained subset of features. Keeping these features corresponds to the value of 1. This operation outputs an ArrayList of integers, which represents the indexes of the features to be used in the denominator.

One embodiment of an algorithm used to arrive at the list of features using PIC normalization is summarized in the following pseudo code:

```
int n_samples=number of spectra in the 2 selected groups;
int n_features=number of features in the feature list;
// Build the list of all features
ArrayList NFList=new ArrayList( )
for (int j=0; j<n_features; j++)
{
   NFList.Add(j);
}
//results in 1, as this is the entire featurelist is in NFList.
Double frac is =FracIonCurrent(f, NFList);
//also results in 1.
Double frac_f=((double)NFList.Count)/n_features;
ArrayList NFList_old=(ArrayList)NFList.Clone( )
//while the fraction of ION current is greater than or equal
//to that specified by the user, and the percentage of used
//features is greater than that specified by the user.
While      (frac_is>=MinAllowedFracOfIC     &&
   frac_f>=MinAllowedFracOfFeatures)
{
   NFList_old=(ArrayLisONFList.Clone( )
   //renormalize based upon the present NFList, then compute
   //the coefficient of variation for each set of normalized
   // features, then sort by the coefficient of variation,
   // the highest coefficient of variation is removed from the
      //NFList.
   OneStep(f, ref NFList);
   //now there is one less feature in the list of indexes,
   //and fraction of ION current may be computed as the result
      of // PIC/TIC
   //where PIC is the sum of all feature values for the //feature
      indexes specified in the NFList. And where //TIC is the
      sum of all feature values.
   Frac_ic=FracIonCurrent(f, NFList);
   //frac f is simply the percentage of spectra being used
      presently //in the NFList
   frac_f=((double)NFlist.Count)/n_features;
}
return NFList_old;
```

Numerous additional minor and major variations in this algorithm will be apparent to one of skill in this art and are contemplated as part of the claimed invention.

Once this calculation is completed, the list of features to use in the partial ion current denominator is determined.

The second operation is to renormalize all the feature values for the specified groups using the partial ion current denominator. First normalization values are arrived at for each spectra/sample using the feature values specified by the list of indices output from the previous operation. Then these normalization values are used to modify the list of feature values specified within the two-dimensional array of feature values.

This function is achieved by performing an algorithm represented by the following pseudo code.

```
Int n_samples=number of spectra in the selected groups;
int n_features=number of features in the feature list;
```

```
//initialize output array.
Double[,] f2=new double[n_samples, n_features];
//array for the normalization values.
Double[ ] norm=new double[n_samples];
// find normalization factors for each sample
for (int I=0; I<n_samples; I++)
{
  norm[I]=0;
  for each (int k in NFList)
  }
  //set norm[I] to sum of all feature values for the
  //feature indices specified in the NFList.
  Norm[I]+=f[I,k];
  }
  //divide by number of specified features.
  Norm[i]/=NFList.Count;
  for (int j=0; j<n_features; j++)
  {
  //normalize by dividing feature values by the normalization
  //value for the specified feature.
  F2[I,j]=f[I,j]/norm[I];
  }

//return result.
Return f2;
```

Numerous additional minor and major variations in this algorithm will be apparent to one of skill in this art and are contemplated as part of the claimed invention.

After these two steps are completed, partial ion current normalization is completed. Partial ion current normalization can lead to a fairly drastic reduction in the CVs of individual peaks. For urine reproducibility data, where one measures the variability of sample pre-processing via fractionation (resin to remove salts), the reduction in CV is about a factor of two.

Figure 7A:
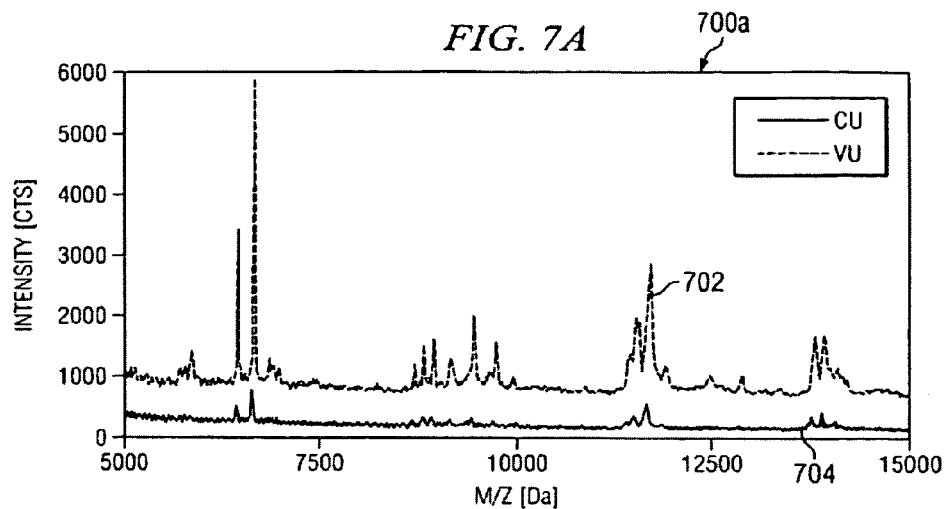
FIG. 7A is a graph showing multiple spectra being completely preprocessed to simplify comparison of the spectra as shown in FIG. 7B.
Figure 7B:
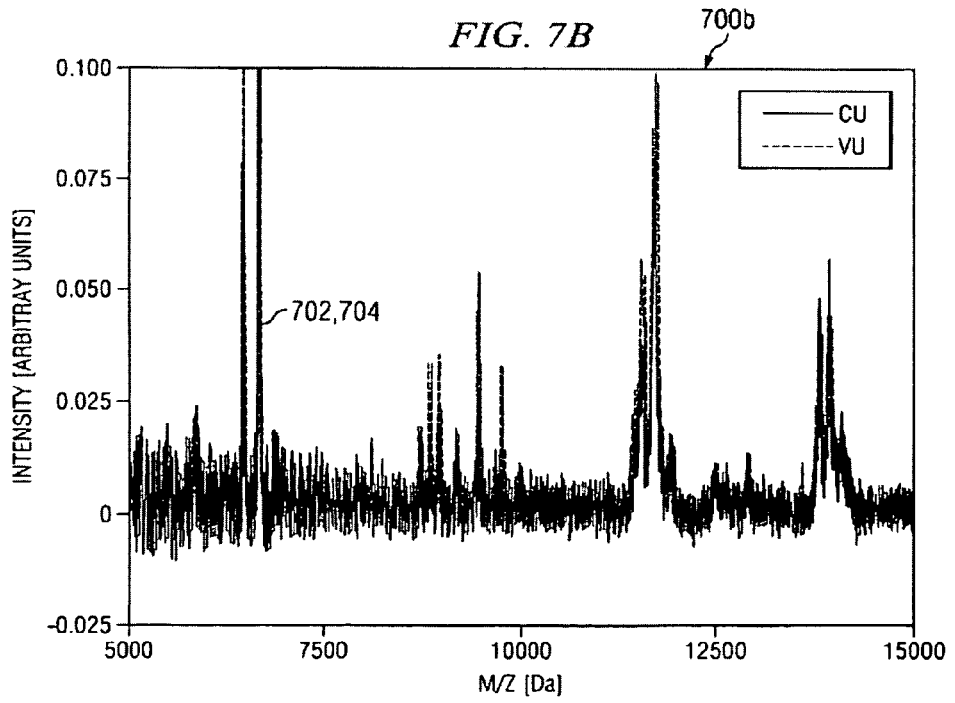

FIG. 7A is a graph 700a showing multiple spectra 702 and 704 being normalized to simplify comparison of the spectra as shown in FIG. 7B. As shown, features (e.g., peaks) of the two spectra 702 and 704 are relatively aligned, but have different amplitudes. This amplitude difference results in the different intensities of the different spectra 702 and 704. By normalizing the two spectra 702 and 704, using partial ion normalization or other normalization algorithm, the two spectral 702 and 704 substantially overlap and can be properly compared as shown in the graph 700b of FIG. 7B.

FIGS. 8A and 8B are graphs 800a and 800b showing multiple sample spectra 802a-802n (FIG. 8A) being aligned 802a'-802n' (FIG. 8B). The absolute mass scale of spectra can vary considerably. Spectra can be shifted with respect to one another, and even the internal mass scale is not constant. In standard proteomics tasks, special compounds are added that give rise to peaks at known m/z values. Spectra can then be recalibrated (i.e., the m/z values may be rescaled according to these external calibrants) and absolute mass accuracies of a few tens of ppms can be achieved in the low mass range, where peptides are expected. In the case of undigested samples, it is sometimes difficult to add calibrants to tissue; and often not desirable, as calibrants could suppress relevant peaks due to ion suppression effects. For spectral comparison, however, it is sufficient to align the spectra to a common mass scale and it is not so important that this mass scale actually corresponds to an absolute measure of mass (i.e., no database searches are performed). Identification of common peaks may be performed, as described with respect to FIG. 9.

In order to align spectra, common peaks may be identified over groups of spectra. Peaks from spectra are put on a line and divisive clustering algorithms may be used to separate this large list into a list of clusters in the following way:

Initialization: peak positions of the spectra are arranged into one ordered list (by m/z value)

First separation stage: Where a minimal separation (typically 30 Da) may be used to split this long list into clusters of peaks, where each individual peak is closer together than the desired minimal separation. As a result, a list of clusters of close peaks may be obtained.

Fine separation: For each of these clusters, a histogram of peak differences may be generated. The cluster at the outlier distance, which is defined as twice the median separation of peaks in the cluster may be split, if the split distance is smaller than twice the peak width or smaller than the instrument resolution at this m/z range, then the clusters are not split. If a split occurs, then the same analysis on the two resulting clusters may be recursively performed until no further splits occur. If no splits occur, then go on to the next cluster.

As a result, a list of clusters that are close in m/z and well separated is obtained. Each cluster can be characterized by its center (the median of the m/z positions of all peaks in the cluster), and its width (the $25^{th}$ and $75^{th}$ percentile of these positions). Alternatively, but less robust, the mean and standard deviation may be used as a measure for the location and spread.

Selection typically in the order of ten clusters of decent average intensity as uniformly spread as possible over the m/z range, may be performed. A linear (quadratic) regression on each spectrum to align the mass scales of all spectra to these common peaks may also be performed. In one embodiment, the following cluster centers may be used: 6434.50, 6632.18, 11686.94, 12864.88, 15131.14, 15871.47, 28102.55

An alignment may be performed with a tolerance of 5000 ppm, i.e., if in any spectrum an alignment point was not found at the specified positions within this tolerance, this point may be ignored. However, if an alignment is not performed, the following are not detected as features: 5764, 8702, 9426, 11443, 11686, 21066, 28102, 28309. As a result, The median standard deviation of features is reduced from 4.63 Da to 3.68 Da for the peaks that are visible in the non-aligned spectra This selection of these common peaks can be used to register spectra to a common m/z scale, as shown in FIG. 8B.

Feature Extraction

Continuing with FIG. 3, a feature extraction process at step 308 is used to extract features (e.g., peaks) from the spectra. In doing so, a determination is made as to which features are to be extracted.

While a visual inspection of spectra, their averages and group differences, provides some guidance on the ability to distinguish various states or clinical stages of disease using mass spectroscopy, a more quantitative analysis may be performed. A differentiating peak is based on the m/z positions of peaks in the spectra. Such a position is a tentative marker if it is common to some user-defined number of spectra within a given group or feature. Once a list of these features is created for each group, each feature can be given a definitional value. Using the peak-width settings of a peak finding algorithm, the normalized and background subtracted amplitudes may be integrated over this range and assigned this integrated value (i.e., the area under the curve between the width of the feature) to a feature. For spectra where no peak has been detected within this m/z range, the integration range may be defined as the interval around the average m/z position of this feature with a width corresponding to the peak width at the current m/z position.

The values of features can vary considerably from spectrum to spectrum, even within the same sample (e.g., serum or tissue), or from within different samples from the same cell type. While the m/z position of the peaks is very reproducible, the amplitudes exhibit sizable fluctuations.

As previously described, a measure for the variation of the feature values is their coefficients of variation (CV). The coefficients of variation are defined as the ratio of the features' standard deviation over their average value. Other definitions are possible, such as the ratio of the percentile range between the $25^{th}$ and $75^{th}$ percentile over their median value. A typical distribution of CV values for the spectra used is provided in a histogram. While there are feature values that are highly reproducible with CV values less than 0.5, the majority of features show a large variation. This emphasizes why extraction is not trivial and fluctuations and distributions of features are to be analyzed before identifying the feature as a potential differentiating peak with a distinguishing characteristic.

Continuing with FIG. 3, a feature selection process is performed at step 310 to select the features that are utilized in performing the classification analysis. The feature selection process may be illustrated as shown in FIG. 9.

Figure 9:
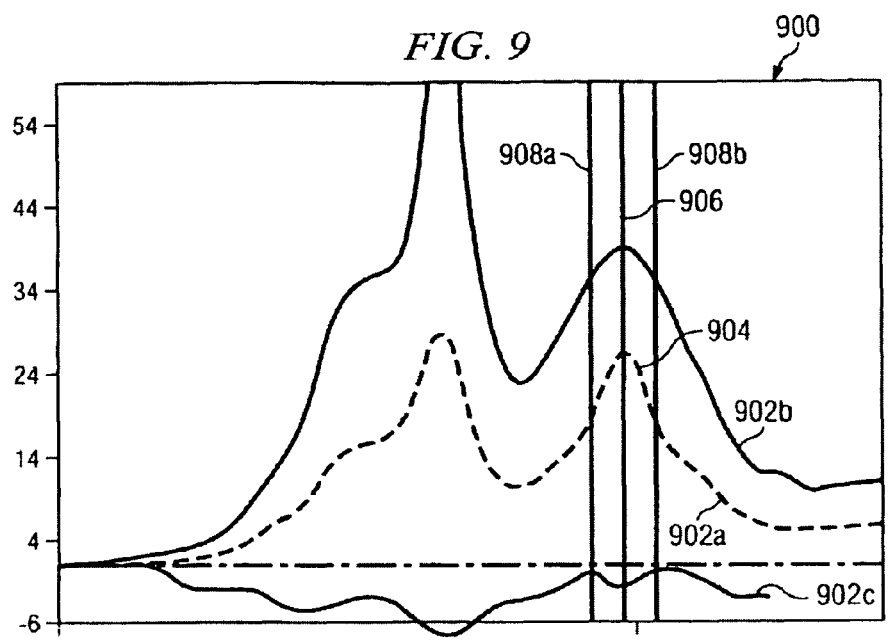
FIG. 9 is a graph of an exemplary process for selecting a feature by locating a peak common in more than x spectra having a certain width.

FIG. 9 is a graph of an exemplary process for selecting a feature (candidate features) by locating a peak common in more than "x" spectra having a certain width, where the width is defined as alignment error plus peak width. Various selection techniques may be utilized in performing the feature selection. As shown, there are three spectra 902a-902c (collectively 902). These spectra 902 are utilized to locate a feature (e.g., peak) 904. As shown, a center vertical line 906 extends through the center of the feature 904, which is common on more than one spectra 902, and side vertical lines 908a and 908b define the width of the feature (alignment error+peak width).

The selection of differentiating features may be performed in a three step process: First, all features are ordered by a univariate p-value obtained from a simple hypothesis test assuming all features are independent. In some implementations, a Mann-Whitney test to obtain a p-value for each feature may be used. Other methods are possible, but less robust, such as two-sample t-tests, Kolomogorov Smirnov tests, or others. Second, using Bonferroni corrections, the top ranked (smallest p-value) features are inspected by comparing group averaged spectra (the average of the spectra in a clinical group). If a feature is not distinguishing groups, it is dropped as a candidate. Third, and in a final step, feature selection may be performed using cross-validation errors as a criterion for success. Various implementations to this effect are outlined below:

The selection of relevant features is more of an issue in gene microarray experiments as there are thousands of features and few samples. Feature selection is also an issue for the identification of biomarkers when examining mass spectral data as there is some evidence that feature selection does not influence the performance of some classifiers very much. Nevertheless, it is difficult to interpret classification results if there are many tens of features, and in reality, there is no expectation that all of these features are relevant.

Ranking of features by their importance may be performed to differentiate various stages of disease. It is straightforward to select one feature at a time, but when there are many tens of features, the task is more difficult to determine which of the features are the important ones for the particular stage of disease. In order to compare biomarkers and spectra across laboratories, the same features are to be identifiable, and those features that appear due to uncertainties in sample preparation, instrument usage, and population variations be distinguishable.

Feature selection faces two algorithmic determinations. The first determination is purely combinatorial. A complete search of all possible combinations of l features of a total of m available (measured) features leads to $$\binom{m}{l} = \frac{m!}{l!(m-l)!}$$

combinations, e.g. for m=20, l=5 this number is 15504. As typically in mass spectra, there are a couple of hundred available features, this number of combinations may be too large for a complete search. Also, it may not be readily apparent which value of l is optimal. Hence, special heuristic search strategies may be used. The second determination arises from the lack of a unique quality measure that decides which feature set is better than another. As one criterion for feature selection could be the classification performance, "wrapper methods" embed feature selection as part of the classification algorithm. These methods use an estimation of the classification error, ideally a measure of the generalization error, which is hard to determine, and is typically approximated by leave-one out cross-validation (LOOCV), or margin based error bounds in the case Support Vector Machines (SVM) learning. Alternatives include filter methods that perform feature selection before classifiers are generated. Each of these approaches has their own issues, and utilizes special handling with respect to validation.

Search strategies are discussed below first, and then a set of quality measures that are commonly used are listed.

Feature Search Strategies

Most search strategies are based on a "divide and conquer" approach, optimizing the feature selection criterion. For specific choices of the feature selection criterion, it may be possible to use probabilistic sampling in the spirit of importance sampling Monte Carlo, or special optimization techniques, such as dynamic programming.

As used, tree-based clustering may start with all features and features may be deleted one-by-one. Alternatively, the process may start with one feature and add other features one-by-one. As an illustration, four features may exist $\{x_1, x_2, x_3, x_4\}$.

Top-Down Search:

Calculate the value of the feature selection criterion for $\{x_1, x_2, x_3, x_4\}$ yielding $C_4$.

Calculate the value of the feature selection criterion for each of $\{x_1, x_2, x_3\}, \{x_1, x_2, x_4\}, x_3, x_4, \{x_2, x_3, x_4\}$, and select the best, say $\{x_1, x_2, x_3\}$ with value $C_3$.

Calculate the value of the feature selection criterion for each of $\{x_1, x_2\}, \{x_1, x_3\}, \{x_2, x_3\}$, select the best, say $\{x_1, x_2\}$ with value $C_2$.

And finally pick the best single feature from $\{x_1, x_2\}$ with value $C_1$.

The best value of $\{C_1, C_2, C_3, C_4\}$ defines the (sub)optimal feature set.

Similarly starting from one feature, and adding more one by one defines a bottom-up search. This does not necessarily give an optimal solution, as there is not a guarantee that the optimal lower (higher) number of features solution evolves according to these trees. One way to improve on these simple procedures is to reconsider features previously discarded, or to discard previously selected features. This algorithm is called the floating search method, as understood in the art, and as follows:

Floating Search Method:

The following describes a search for a fixed number l of m features. A loop over l may be performed to optimize for the number of features. The floating search method is based on either top-down or bottom-up searches. The algorithm described is based on the bottom-up method.

Consider a set of m features. The idea is to search for the best subset of k of them for k=1, 2, ..., l≦m optimizing C. Let $X_k=\{x_1, \ldots x_k\}$ be the optimal set for k features, and $Y_{m-k}$ the set of the remaining m-k features. The lower dimensional best subsets $X_2, X_3, \ldots, X_{k+1}$ of 2, 3, ..., k−1 features are kept in storage. At the next step the (k+1)th optimal subset $X_{k+1}$ is formed by taking an element of $Y_{m-k}$. Then, a check is performed through all lower dimensional subsets as to whether this improves on C, and replaces the previously selected feature. The algorithm runs as follows (C is such that bigger is better):

Select the best single feature, yielding $X_1$ with $C_1$.
Add another one based on C, yielding $X_2$ and $C_2$.
Now iterate over k:
Step I, Inclusion: Choose that element from $Y_{m+k}$ which combined with $X_k$ gives the best C, i.e. $X_{k+1}$=arg $\max_{y \in Y_{m-k}} C(X_k,y)$ defining $X_{k+1}\{X_k,x_{k+1}\}$ as in the bottom-up algorithm.
Step II, Test:
1. Find the feature $x_r$ that has the least effect on the cost C when removed from $X_{k+1}$, i.e. $x_t$=arg $\max_{x_s \in X_{k+1}} C(X_{k+1}/\{x_r\})$.
2. If r=k+1, k=k+1, $C_{k+1}$=C and go to Step I.
3. If r≠k+1 and $C(X_{k+1}/\{x_r\})<C_k$ go to Step I, i.e. if removal of $x_r$ does not improve on the previously selected group do not do a backward search.
4. Special case for k=2: If k=2 set $X_2=X_3/\{x_r\}$ and $C_2=C(X_3/\{x_r\})$.
Step III, Exclusion (backward search):
1. $X_k'=X_{k+1}/\{x_r\}$ i.e. remove $x_r$.
2. Find the least significant feature $x_s$ in the new set via $s_s$=arg $\max_{y \in X_k'} C(X_k'/\{y\})$.
3. If $C(X_k'/\{x_s\})<C_{k-1}$ then $X_k=X_k'$, reset $C_k$ and go to step I terminating the backward search.
4. Set $X_{k-1}'=X_k'/\{x_s\}$ and k=k−1.
5. Special case k=2: Set $X_2=X_2'$ and $C_2=C(X_2')$ and go to Step I.
6. Go to Step III.

This algorithm generally operates substantially better than the simple bottom-up algorithm, and it can be run up to m to again pick up the maximal (minimal) criterion set.

Random Feature Selection Algorithms

The random feature selection algorithm is an optimization strategy based on counting the frequency of configurations from random sampling. For example, in building hierarchical agglomerative clusters from some initial configuration (k-medians, k-means, fuzzy clustering), the algorithm can be started many times over, store the individual configurations from each run, and build a frequency histogram. This can often be combined with cross-validation.

Classifier Generation

Continuing with FIG. 3, at step 312, classifier generation is performed. The classifier generation may include a few functions, including (i) supervised learning, (ii) cross validation, and (iii) blind classification or testing. The first two functions, supervised learning and cross validation, may be performed on the raw spectra with associated known clinical results 108 provided by the cancer research clinics 104, as described in FIG. 1.

While feature ranking gives some idea about the importance of features for discriminating groups, a more thorough analysis uses in a supervised learning procedure. Supervised learning is the process, by which category labels are provided for each instance, in a training set (i.e., each spectrum) and seeks to reduce the number of misclassifications. Another, more specific, definition of supervised learning is the mapping from a high-dimensional feature space to label space from feature/differentiating peak expression to disease label or response label (otherwise designated as class label): The label is a function of the mass spectrometer peaks and associated parameters. A researcher or other person having spectra from, and clinical information about, the cancer patient from whom the spectrum was produced may perform the supervised learning process. The process may be performed by using standard algorithms from the theory of supervised learning. The output of supervised classification algorithms is a classifier algorithm (dependent on the training set) that generates a class label for a new instance or spectrum. In one embodiment, a k nearest neighbors (KNN) algorithm may be utilized for the classification.

K Nearest Neighbors Algorithm

The k-nearest-neighbor method is a simple method of density estimation. The probability that a point x' falls within a volume V centered on x is:

$$p \Box \int_V dx\, p(x)$$

For a small volume $p \Box p(x)V$. The probability can be approximated by the proportion of samples falling within the volume V. Hence, if k is the number of samples out of a total of n that fall within V then $$p \Box \frac{k}{n} \text{ and } p(x) = \frac{k}{nV}$$

The k-nearest-neighbor approximation is to fix the probability k/n (or, for a fixed number of samples to fix k) and to determine the volume that contains k samples. This is in contrast to histogram estimates where the bin width is fixed, and the number of points is counted. There are some issues with the regularity of this definition, but it can be shown to be unbiased and consistent if $$\lim_{n \to \infty} k(n) = \infty$$

and $$\lim_{n \to \infty} k(n)/n = 0.$$

A decision rule can be constructed in the following way. Suppose that there are $k_m$ samples in class $\omega_m$, and the total number of $\omega_m$ samples to be $n_m$. Then, the class-conditional probability is:

$$p(x|\omega_m) = \frac{k_m}{n_m V}$$

The prior is $n_m/n$ (if there n samples in total over all classes).

The Bayesian decision rule is to assign x to $\omega_m$ if $$p(\omega_m|x) \geq p(\omega_i|x) \forall i$$

and using Bayes theorem this results in this selection $$\frac{k_m}{n_m V}\frac{n_m}{n} \geq \frac{k_i}{n_i V}\frac{n_i}{n} \forall i \Rightarrow k_m \geq k_i$$

In the case of a tie, a tie breaker may be made via the nearest mean, closest member, or otherwise. Alternatively, the tie breaker may be restricted to odd k. Small k leads to irregular surfaces while large k to smooth surfaces. The asymptotic misclassification rate is bounded from above by twice the Bayes error, which is a very good asymptotic performance for such a simple algorithm. KNN classification lends itself to the use of prototypes, i.e., a data condensation technique. But here, the use of KNN classification is more used for the reduction in necessary storage. The choice of a distance function may be utilized. Alternatively, Euclidean differences, which is not optimal, may also be utilized. The voting process for a simple example of a two-dimensional features space is illustrated in FIG. 11.

Figure 11:
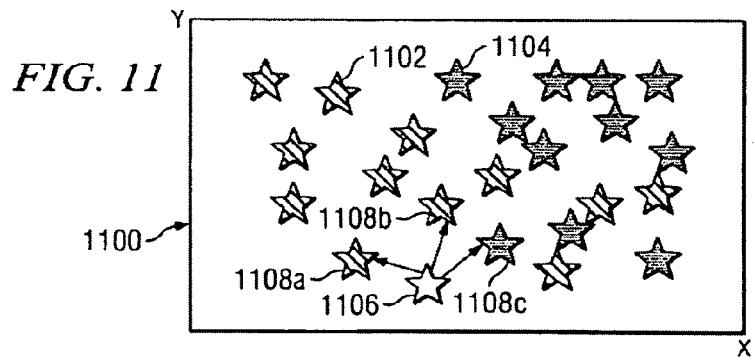
FIG. 11 is a graph showing an exemplary group of class labeled spectra indicia representative of two different classes of disease progression and a test spectrum indicia to be classified.

FIG. 11 is a graph 1100 showing an exemplary group of class labeled spectra indicia representative of two different classes of disease progression and a test spectrum indicia to be classified. To graphically represent differentiating peaks in feature space, in this illustration a two-dimensional feature space, the graph 1100 is a two dimensional graph having an x-axis and a y-axis. If the feature space were a 12-dimensional feature space (i.e., 12 features or peaks were selected as differentiating peaks indicative of distinguishing characteristics that classified a spectrum to be class labeled as "good" or "bad"), then it would not be possible to easily graphically represent the spectra, so a two-dimensional feature space is utilized as an example.

In this case, the spectra are classified with class labels as "good" 1102 and "bad" 1104, where the "good" class labeled spectra indicia 1102 are represented on the graph 1100 as one pattern and the "bad" class labeled spectra indicia 1104 are represented as another pattern. As previously described, class labeled spectra may be developed from a cancer research clinic and used as a control sample for classification purposes based on the clinical results of a cancer patient in responding to an anti-cancer drug, such as Iressa. A test spectrum indicia 1106 may be placed on the graph. 1100 in a location representative of a test spectrum from a new cancer patient for whom a treatment plan is being determined. The location of the test spectrum indicia 1106 is based on the amplitudes of the two features. (i.e., the x and y amplitudes). As shown, and in accordance with the probability KNN algorithm, the closest three class labeled spectra indicia 1108a, 1108b, and 1108c are potential candidates for the test spectrum to be associated.

An exemplary probability test for the classification process for a test point of the two-dimensional feature space is:

$$P(\vec{x} \in A) = \frac{k_A + 1}{k_A + k_B + 2} {}_2F_1\left(1, k_B + 1, k_A + k_B + 3, 1 - \frac{N_A}{N_B}\right)$$

If the probability difference between two classes exceeds a certain user supplied threshold delta-p, then the probability can be considered significant and a classification of "good" or "bad" can be made. If the probability difference is below a certain threshold, then a classification of "undetermined" can be made.

While a KNN algorithm may be utilized as a classifier algorithm, other classification algorithms may be utilized. Another algorithm developed in accordance with the principles of the present invention is a probabilistic k nearest neighbor algorithm, which is a modified KNN algorithm that provides additional flexibility and provides more information for clinical applications.

Modified (Probabilistic) k Nearest Neighbor Algorithm

In accordance with the principles of the present invention, a modified k nearest neighbors algorithm may be used for classification. In its simplest implementation, the modified KNN algorithm searches for the k nearest neighbors in feature space and assigns a class label according to a simple majority vote over the labels of these nearest neighbors. Feature space is defined as being the number of features (e.g., 12 features) that are being used to define a spectrum. In one embodiment, there is no explicit training phase and all instances are used in the classification of spectra. Usually just simple Euclidean distances are used to determine the neighbors, but other definitions are possible (e.g. Mahanolobis distances from suitably defined covariance matrices).

In the traditional K-nearest neighbors (KNN) framework, classification is performed as follows:

Each object, or instance, to be classified (here—the mass spectrum) is characterized by d numbers $x_i$, I=1 . . . D (here—the values of d features), and is thus represented by a point in d-dimensional space. The distance between the two instances is defined by the usual Euclidian metric $$\sqrt{\sum_i (x_i - x_i')^2}.$$

Of course, any similarity metric may be used here as well. Additionally, an implementation may use a winsorized Mahalanobis distance in determining the distance between two spectra.

A training set may include instances with known class assignments. Given the training set and a positive odd integer k, classification of the test object is performed as follows:

1. In the training set, find k nearest neighbors of the test object (i.e., spectrum) in the d-dimensional space.
2. Each of these k neighbors belongs to one of the classes. (e.g., good or bad). Find which class has the largest number of representatives.
3. Classify the test object as belonging to this class.

This KNN classification has two drawbacks. First, it provides no information on the confidence of class assignment. It is intuitively clear that in the case of k=15 and two classes, the confidence of class assignment in 15:0 situation is much higher than in the 8:7 situation. In clinical applications, it is characterize in the confidence level of each individual class assignment is relevant and used to diagnose patients. In fact, this level may be defined at the outset.

Second, it does not properly take into account the number of instances of each class in the training set. Just adding more instances of the given class to the training set tends to bias classification results in favor of this class.

To correct for these problems, a "probabilistic KNN" classifier has been developed that starts from the information on the classes of k nearest neighbors from the training set, but instead of class assignment produces probabilities of the test instance belonging to each of the classes. Below is a concise description of the reasoning and derivation of the main formulas for probabilistic KNN.

The KNN approach to classification of spectrum samples can be viewed as follows: consider a ball of a certain radius in the d-dimensional space and centered at the test instance. The radius of the ball is determined by the requirement that it contains exactly k instances from the training set. Then observe how many members of each class are among these k instances, and use this information to assign the class label (in the standard approach), or compute probabilities of the test instance belonging to this or that class (in the probabilistic approach).

The training set may be a sample drawn from some (unknown) probability distribution. More accurately, for each class, the subset of the training set belonging to the class is considered to be a sample drawn from the corresponding probability distribution, which is different for each class.

Consider the ensemble of training sets drawn from the same probability distribution. In the KNN approach to classification, the radius of the ball around the test instance is different for each realization of the training set to ensure that it always contains exactly k nearest neighbors. See also the description of the KNN method in the previous section.

The following approximations may be made:
1. The ball around the test instance may be considered fixed, which means, it is dependent of the position of the test instance and on the probability distributions from which the training set is drawn, but the same for each realization of the training set. This approximation is valid when k is not too small.
2. For each class, the number of instances of this class within the ball is drawn from the Poisson distribution. This approximation is valid when the ball contains only a small fraction of the overall probability for this class.
3. The probability densities for the classes are approximately constant within the ball.

Consider the case of two classes. Each instance is represented by a point $\bar{x}$ in d-dimensional space. The full d-dimensional space is denoted by $\Omega$.

Class 1 is characterized by the probability distribution $p_1(\bar{x})$, $$\int_\Omega p_1(\bar{x})d\bar{x} = 1.$$

Class 2 is characterized by the probability distribution $$p_2(\bar{x}), \int_\Omega p_2(\bar{x})d\bar{x} = 1.$$

A training set may be formed of $N_1$ points drawn from class 1, and $N_2$ points drawn from class 2. The vicinity of the test point may be denoted by $\omega$. This is actually a ball centered at the test point, but this is irrelevant for the following. For a given realization of the training set, there are $k_1$ points in $\omega$ from class 1 and $k_2$ points in w from class 2. It is assumed that $k_1 \ll N_1$, $$\int_\omega p_1(\bar{x})d\bar{x} \ll 1.$$

The same is true for class 2.

This ensures the validity of the Poisson approximation: $k_1$ comes from the Poisson distribution with the expectation value $\lambda_1$, $$\lambda_1 = N_1 \int_\omega p_1(\bar{x})d\bar{x};$$

$k_2$ comes from the Poisson distribution with the expectation value $\lambda_2$, $$\lambda_2 = N_2 \int_\omega p_2(\bar{x})d\bar{x}.$$

Now the test point (the center of $\omega$) is treated as "yet another point." In other words, there are $k_1+k_2+1$ points in $\omega$, rather than $k_1+k_2$, and it is not known in which class the test point belongs. The probabilities of the test point belonging to class 1 and class 2 may be assigned as follows:

$$\frac{p(\text{class}1)}{p(\text{class}2)} = \frac{\int_\omega p_1(\bar{x})d\bar{x}}{\int_\omega p_2(\bar{x})d\bar{x}}$$

Thus $$p(\text{class}1) = \frac{\int_\omega p_1(\bar{x})d\bar{x}}{\int_\omega p_1(\bar{x})d\bar{x} + \int_\omega p_2(\bar{x})d\bar{x}} = \frac{\frac{\lambda_1}{N_1}}{\frac{\lambda_1}{N_1} + \frac{\lambda_2}{N_2}}$$

By treating the test point (the center of $\omega$) as "yet another point," it is implicitly assumed that both $p_1(\bar{x})$ and $p_2(\bar{x})$ do not change significantly within co.

The problem is that $\lambda_1$ and $\lambda_2$ are actually unknown. Their probabilities, however, can be estimated in the Bayesian manner. Both $k_1$ and $k_2$ are assumed to obey the Poisson distribution, $$p(k|\lambda) = \frac{\lambda^k}{k!}e^{-\lambda}.$$

Denoting the prior distribution for $\lambda$ by $p_0(\lambda)$, $$p(k) = \int d\lambda p(k|\lambda)p_0(\lambda).$$

By the standard Bayesian reasoning, $$p(\lambda|k) = \frac{p(k|\lambda)p_0(\lambda)}{\int d\lambda p(k|\lambda)p_{0\Xi}(\lambda)}.$$

Assuming from now on the flat prior distribution of $\lambda$, $p_0(\lambda)=1$, the following can be obtained $$p(\lambda|k) = p(k|\lambda) = \frac{\lambda^k}{k!}e^{-\lambda}.$$

Eventually, the following is obtained $$p(class1) = \int_0^\infty d\lambda_1 \int_0^\infty d\lambda_2 \frac{\lambda_1}{\lambda_1 + \frac{N_1}{N_2}\lambda_2} p(\lambda_1)p(\lambda_2),$$

where $$p(\lambda_1) = \frac{\lambda_1^{k_1}}{k_1!}e^{-\lambda_1},$$

$$p(\lambda_2) = \frac{\lambda_2^{k_2}}{k_2!}e^{-\lambda_2}.$$

Computation of these integrals gives the following:

$$p(\text{class1}) = \frac{k_1+1}{k_1+k_2+2} {}_2F_1\left(1, k_2+1, k_1+k_2+3, 1-\frac{N_1}{N_2}\right).$$

For the equal sizes of the samples used in the training set ($N_1=N_2$) this simplifies to the following:

$$p(\text{class1}) = \frac{k_1+1}{k_1+k_2+2},$$

$$\frac{p(\text{class1})}{p(\text{class2})} = \frac{k_1+1}{k_2+1}.$$

For more than two classes and different samples sizes in the training set, it is difficult to obtain p(class I) in closed form. In this case, the following much simplified estimate may be used:

$$\frac{p(\text{class } i)}{p(\text{class } j)} = \frac{k_i+1}{k_j+1} \cdot \frac{N_j}{N_i},$$

Or, equivalently, each p(class I) is proportional to $$\frac{1}{N_i}(k_i+1),$$

while $$\sum_{i=1}^{N_{classes}} p(class\ i) = 1$$

The parameter characterizing the robustness of results to faulty spectra is a user-supplied parameter, p-diff, that defines how different the class probabilities have to be in order to associate a label with a spectrum. For example, if p-diff is set to 0.1 and the probability for class A is 0.6 and for class B is 0.4, then the difference 2 is greater than 0.1, and class A will be chosen. If, on the other hand the class probability for class A is 0.52 and for class B is 0.48, then the difference 0.04 is smaller than 0.1, and the classifier returns a class label as being "Undefined."

Alternatively, hypothesis testing may have the classification be significant with an externally specified significance $\alpha$. In a standard hypothesis test formulation, the classification can be described as follows:

Data: A test instance may include two classes A and B, $k_A$ and $k_B$ nearest neighbors of class A and class B, and the populations of $N_A$ instances of class A and $N_A$ instances of class B.

Test Statistic Just simply the number of neighbors in class A:

T=$k_A$

Null distribution: The null is assumed to be the number of A neighbors that is expected from the population ratios alone, i.e. $k_A$ under the null is a binomial random variable with the parameters $k=k_A+k_B$ and $p^*=N_A/N_B$.

Hypothesis: (two-tailed) This is an implementation of a binomial test, as understood in the art.

$H_0$:$p_A$=$p^*$ $H_1$:$p_A \neq p^*$

In the test development case, the number of nearest neighbors is rarely larger than twenty so the use the normal approximation is not used. For a given overall significance $\alpha$ is solved from a table (or run a computer) $P(Y \leq t_1)=\alpha_1$ and $P(Y \leq t_2)=1-\alpha_2$ for $t_1$ and $t_2$, where Y is a binomial random variable as defined under the null, and where $\alpha_1$ and $\alpha_2$ are approximately to $\alpha/2$ and add up to $\alpha$. The rejection regions are the values of T less than $t_1$ or greater than $t_2$. Confidence regions may also be estimated for $p^*$ following the procedure outlined in the section Binomial test.

While the modified KNN algorithm may be utilized as the classification algorithm as described above, alternative classification algorithms may be utilized in accordance with the principles of the present invention. Such classification algorithms may include fuzzy KNN, Kernel methods (e.g., SVM), unsupervised classification, spectral clustering, kernel PCA, non-parametric clustering, k-Means, k-Histograms, hierarchical clustering, and random forests, for example. These classification algorithms provide the ability to classify a spectrum in accordance with class labeled spectra (e.g., spectra that has been classified and labeled from a control group of cancer patients), but lack the transparency and ease of use of the above described KNN algorithms.

Continuing with FIG. 3, step 312, learning may be utilized in generating classifiers for a training set of spectra. In the case of sampling serum for detecting whether an anti-cancer drug will be effective on non-small-cell lung cancer, control groups of patients were utilized, including using three sets of patients whose cancer progressed following chemotherapy. Each of the patients was treated with Iressa and information, including survival times, of these patients was recorded. The control samples were from patients of less severe cases (cancer stages III and IV) that did not receive treatment with EGFR-K1 inhibitors and serum was produced during the treatment. A summary of data sets used in several studies is provided in TABLE III. Each data set represents the cancer research center from which spectra and associated patient information was received.

TABLE III

Data Sets Used in Study

Figure 12:
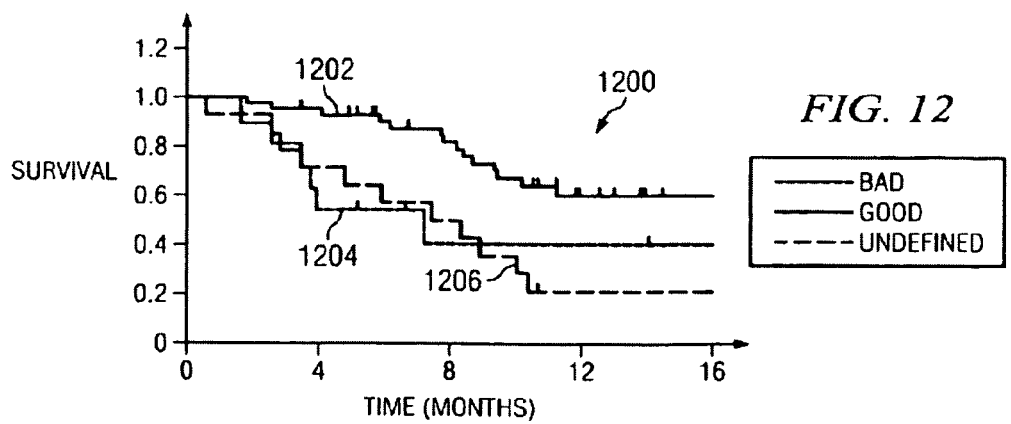
FIG. 12 is a Kaplan-Meier plot of test data showing survival rates of groups of patients as classified in accordance with the principles of the present invention as obtained from using Italian samples as a training set and Japanese samples as a test set.
Figure 13:
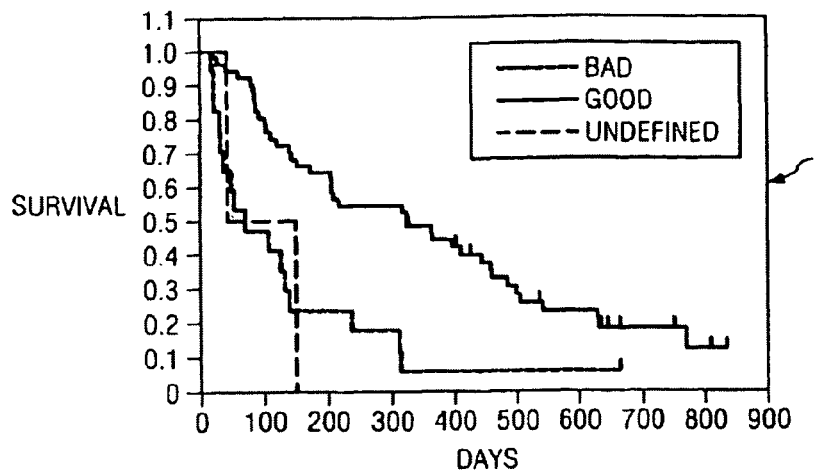
FIG. 13 is a Kaplan-Meier plot of test data showing survival rates of groups of patients as classified in accordance with the principles of the present invention as obtained from using the Japanese samples as a training set and the Italian samples as a test set.
Figure 14:
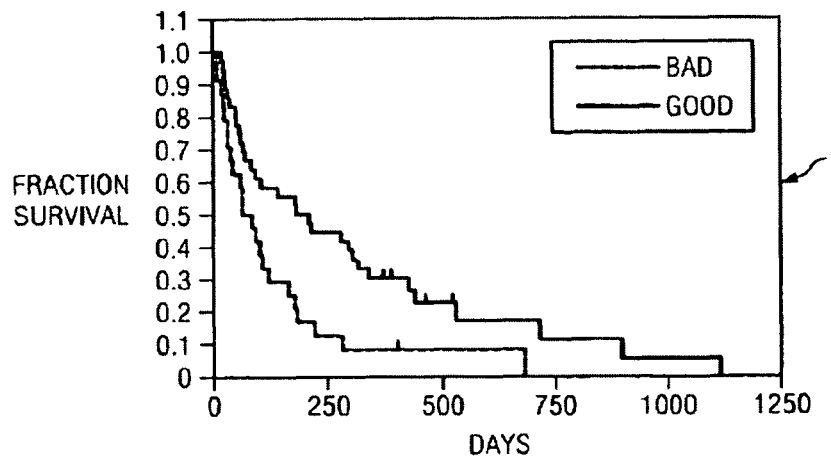
FIG. 14 is a Kaplan-Meier plot of test data showing survival rates of groups of patients as classified in accordance with the principles of the present invention as generated by a classifier algorithm for a fully blinded set of samples.

| Data Set | Size | Patient Data | Use |
|---|---|---|---|
| Italian 1 | 70 | Complete | Training Set for FIG. 12, test set for FIG. 13 |
| Japan 1 | 43 | Prognosis, Survival | Training set for FIG. 13, test set for FIG. 12 |
| Japan 2 | 26 | Prognosis, Survival | Training set for FIG. 13, test set for FIG. 12 |
| VUMC | 100 | Survival | Control Set |
| Italian 2 | 69 | Survival | Fully blinded test set for FIG. 14 |

TABLE III is a summary of the data set attributes used in a study to determine whether a classifier algorithm could be effective in determining whether a cancer patient would be responsive to Iressa. Data sets Italian 1, Italian 2, Japan 1, and Japan 2 were treated with Iressa following sample collection. Training and testing in the development phase was done crosswise from the Italian 1 sets and the two Japanese sets. The patient data included survival data, where the Italian set had very complete patient history together with treatment and cancer type, the Japanese sets only included prognostic information relating to the WHO definitions of clinical labels, including stable disease (SD), progressive disease (PD), and partial responders (PR) measured by CT imaging. Once the classifier was established, a fully blinded test was performed on the Italian 2 set.

Figure 10A:
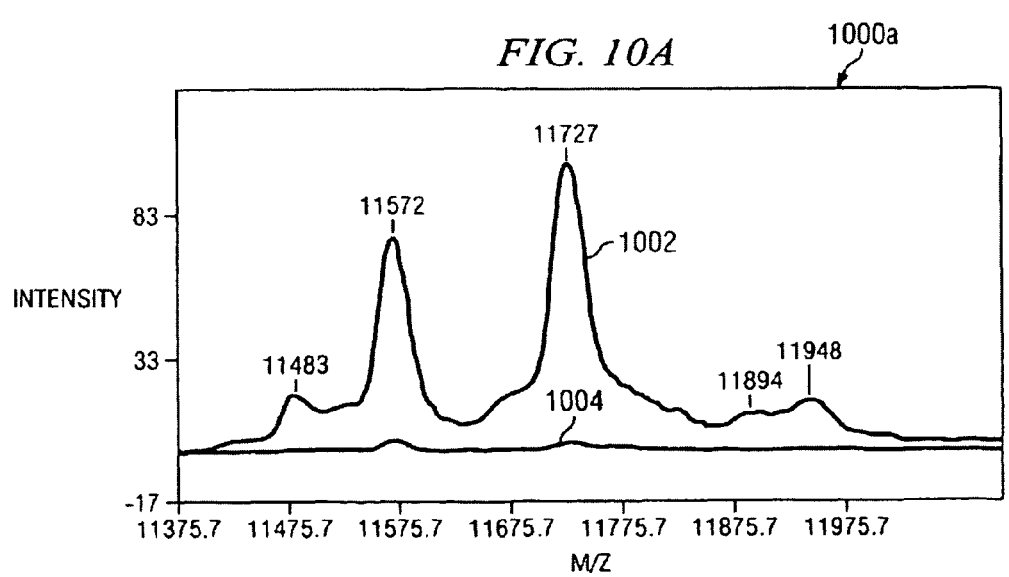
FIG. 10 is a graph representative of the average spectra in clinical groups PD, PD-early, PR, SD-short, and SD-long averaged over all the available test development samples in their respective groups.

FIG. 10A is a graph 1000a representative of an exemplary process for classifying a test spectrum in relation to a group of class labeled spectra in accordance with the principles of the present invention. A test spectrum is considered to have a relation to a class labeled spectra if it is determined by a classifier that the test spectrum is to be class labeled the same as at, least one class labeled spectrum from the class labeled spectra. The curves are group averaged spectra. As shown, there is a cluster of differentiating peaks around 11700 Daltons (Da) used in the classification. The differences between the groups are between the fine clinically labeled groups PD-early 1002 and SD-long 1004 spectra averages. Although not shown, there are 11 differentiating peaks used to construct a classifier (i.e., classifier algorithm using the modified k-nearest neighbor classifier) from the Italian data set (TABLE III) and its parameters are optimized using cross-validation. It is clear in comparing the two group averaged spectra that a presence of biomarkers resulting in the differentiating peaks in spectra of patients with fast progression cancer (PD-early 1002) is nearly absent in those patients that survive a long time and classified with SD-long cancer (SD-long 1004).

Figure 10B:
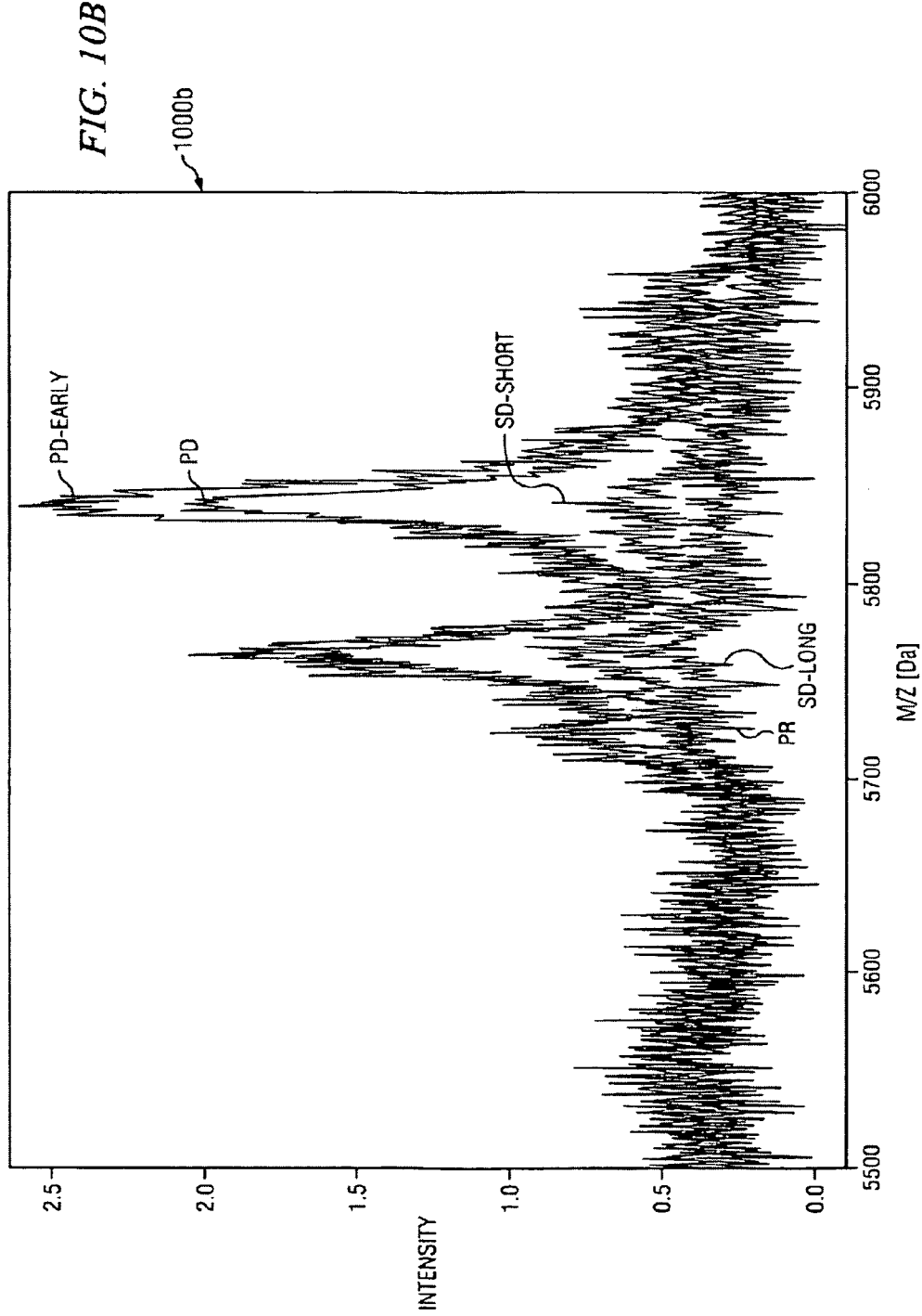
Figure 10C:
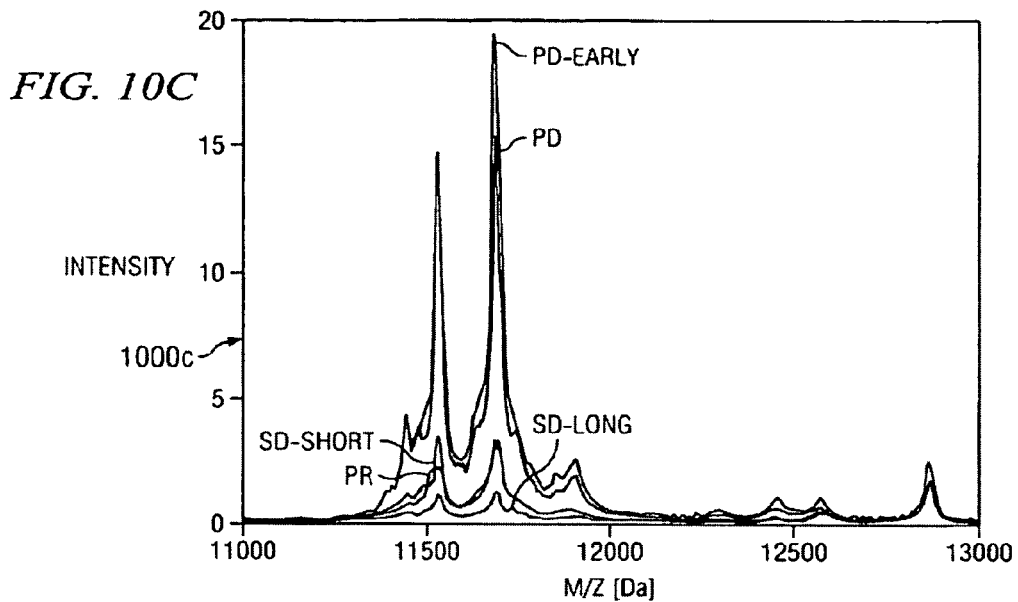

FIGS. 10B and 10C are graphs 1000b and 1000c showing exemplary plots from Italian and two Japanese training sets. In FIG. 10B, the graph 1000b ranges from 5500-6000 Da and FIG. 10c, the graph 1000c ranges from 11000-13000 Da. As shown in these two graphs 1000a and 100b, many differentiating peaks between the different groups are shown. The plots of the groups are averaged, over each group of spectra. That is, the plots are not of individual spectrums.

The unusual fine classification of the standard differentiating peaks is indeed reflected in the strength of the indicated differentiating peaks. A list of the differentiating peaks used is shown in TABLE IV. TABLE V is the same list of differentiating peaks as TABLE IV, but also includes values of features containing group averages of the feature values for the discovery phase samples (Italian 1, Japanese 1 and 2). One set of dominant clusters is shown as group averages in FIG. 10. It should be understood that the differentiating peaks shown are exemplary and that the same or other differentiating peaks may be utilized in accordance with the principles of the present invention to predict cancer patient responders of the drug Iressa. Still yet, if predictions for other anti-cancer or other drugs were to be made, differentiating peaks other than those listed may be utilized for such predictions.

The optimal k-NN classifier results in one leave-one-out cross-validation (LOOCV) error, while 6 of 26 spectra could not be classified. By increasing the requirements for the probabilistic k-NN classifiers, it is possible to move this mislabeling to the case of one unclassifiable spectra. If it is reasonably assumed that the fine classification is correlated to prognosis, PD-early cases being the worst progression and SD-long cases being the longest stable diseases, it can tentatively be concluded that it is possible to obtain prospective drug response information from pre-treatment serum spectra.

TABLE IV

List of Differentiating Peaks

| mz_center | mz_low | mz_high | width = mz high − mz low |
|---|---|---|---|
| 5763.791 | 5732.131 | 5795.45 | 63.3 |
| 5843.241 | 5811.097 | 5875.384 | 64.3 |
| 6433.973 | 6398.186 | 6469.759 | 71.6 |
| 11445.75 | 11376.15 | 11515.34 | 139.2 |
| 11529.52 | 11459.32 | 11599.73 | 140.4 |
| 11685.37 | 11614.03 | 11756.71 | 142.7 |
| 11759.16 | 11687.28 | 11831.04 | 143.8 |
| 11903.24 | 11830.31 | 1976.18 | 145.9 |
| 12452.38 | 12375.37 | 12529.4 | 154 |
| 23354.35 | 23183.57 | 23525.13 | 341.6 |
| 23451.25 | 23279.53 | 23622.97 | 343.4 |
| 66702.45 | 65902.02 | 67502.88 | 1600 |

TABLE V

List of Differentiating Peaks Containing Parameters of Feature Values

| m/z | Value (Good) | Std (Good) | Value (Bad) | Std (Bad) | Width |
|---|---|---|---|---|---|
| 5763.791 | 25.387 | 11.038 | 113.79 | 129.02 | 63.3 |
| 5843.241 | 22.617 | 11.595 | 120.27 | 199.13 | 64.3 |
| 6433.973 | 402.09 | 142.69 | 397.01 | 165.53 | 71.6 |
| 11445.75 | 22.334 | 16.645 | 353.57 | 756.68 | 139.2 |
| 11529.52 | 36.524 | 39.911 | 951.3 | 1401.1 | 140.4 |
| 11685.37 | 40.505 | 43.465 | 1019.9 | 2135.8 | 142.7 |
| 11759.16 | 29.745 | 22.773 | 341 | 472.6 | 143.8 |
| 11903.24 | 20.727 | 9.2393 | 158.1 | 290.08 | 145.9 |
| 12452.38 | 16.825 | 10.226 | 73.804 | 83.106 | 154 |
| 23354.35 | 31.089 | 12.447 | 63.381 | 39.39 | 341.6 |
| 23451.25 | 28.718 | 13.185 | 55.475 | 31.4 | 343.4 |
| 66702.45 | 342.98 | 250.02 | 369.86 | 203.21 | 1600 |

In testing the classifier algorithm, response markers for Iressa can be made with the following associations: SD and PR cases are grouped together in a group having a class label of "good," and PD cases are class labeled as "bad." The classifier developed from the fine classification above was then, again, associating "good" with SD-long and "bad" with PD-early. This classifier was then applied to the Japanese cases (TABLE I), where 18 of these spectra could not be classified, leaving 51 spectra for classification. Of these 51 spectra, 37 had class label "good," and 14 had class label "bad." The test results are summarized in TABLE VI:

TABLE VI

| | Class Labels | |
|---|---|---|
| Test result | Original class label "good" | Original class label "bad" |
| "good" | 32 | 6 |
| "bad" | 5 | 8 |

This test has a sensitivity of 90% and a specificity of 57%. For the purposes of using Iressa, 6 cases, where there was no response, i.e. "bad," were labeled as having a response, yielding a positive predictive value of 0.84. Similarly, 5 cases were mislabeled as "bad," yielding a negative predictive value of 0.61.

To summarize, using a serum based mass spectrometer test to filter non-responders from responders in the Japanese population increases the response rate of Iressa from 65% to 90%, while 5 of 51 patients, who might have benefited from Iressa would be left out. Of these 5 patients, one was labeled SD and 4 were labeled PR. In general, the classification to PD is worst due to a high variability in this group. This does not influence the selection of the "good" cases, but results in the low specificity. This increase indicates that a practitioner could obtain unexpectedly better predictions of the prognosis of using Iressa early in the treatment stage for a certain group of patients. For these patients, Iressa could be continued while patients predicted to have a poor prognosis could be switched to an alternative anticancer therapy. This permits a better long term survival rate since the earlier an alternative anticancer therapy is utilized the more likely it will lead to a beneficial effect.

Continuing with FIG. 3, step 312, blind testing of the classifier may be performed. This means that the classifier algorithm uses the class labeled spectra for classifying test spectra (e.g., from new cancer patients) to determine whether the cancer patient having the same cancer as the cancer patients from the class labeled spectra will respond to the anti-cancer drug. Using the probabilistic KNN classifier, as described hereinabove, the classifier may be generated. Resulting from the classifier may be three potential class labels, "good," "bad," or "undefined." A class label or classification of "good" means that the classifier, in processing the test spectrum, determines the test spectrum to be in the same group as the "good" group of class labeled spectra. The results of such a blind test are shown in FIG. 14, and confirm the results of the development phase.

At step 314 of FIG. 3, and as previously described, visualization may be performed, where the visualization may include tools to perform (i) averaging spectra, (ii) spectral varying, and (iii) feature locating. These visualization tools may be useful for diagnostic purposes.

If it is determined by the classifier that the test spectrum is most closely related to the "good" group of spectra, then the test spectra will be classified as "good" and the patient may be prescribed the anti-cancer drug with a certain level of confidence that he or she will respond. If it is determined by the classifier that the test spectrum is most closely related to the "bad" group of spectra, then the test spectra will be classified as "bad" and the patient will not be prescribed the anti-cancer drug. If it cannot be determined that the test spectrum is associated with either the "good" or "bad" group of class labeled spectra, then the test spectrum will be classified "undetermined" and the patient will not be prescribed the anti-cancer drug.

TABLE VII presents another exemplary set of average differentiating peak values, similar to those of TABLE V, as determined by the feature extraction and selection algorithms in steps 308 and 310 of FIG. 3. These spectra are classified and labeled by the classifier of step 312 of FIG. 3 as "good," "bad," or "undefined." As listed, the "bad" spectra have differentiating peaks that have large standard deviations, typically greater than the amplitude of the peak, such that the peak cannot be measured. The spectra classified as "good" have differentiating peaks that tend to have smaller amplitudes and standard deviations. The "undefined" spectra are somewhere in the middle with the amplitudes of the differentiating peaks being small over certain m/z locations and higher over others.

TABLE VII

| Exemplary Differentiating Peaks and Standard Deviations | | | | | | |
|---|---|---|---|---|---|---|
| Group/MZ | 579438 | 5868.02 | 11483.44 | 11572.81 | 11729.95 | 12495.04 |
| Bad | 190.83 ± 207.43 | 232.88 ± 301.35 | 798.03 ± 964.81 | 1451.46 ± 1541.45 | 1747.09 ± 2208.33 | 97.96 ± 109.81 |
| Good | 8.74 ± 03.69 | 6.40 ± 4.34 | 6.06 ± 6.21 | 15.34 ± 17.77 | 20.15 ± 19.91 | 2.68 ± 4.50 |
| Undefined | 17.62 ± 06.76 | 16.62 ± 07.94 | 37.84 ± 20.51 | 89.82 ± 47.87 | 105.52 ± 53.71 | 8.1 ± 6.08 |

The level of confidence is based on the probability of association with the training set of spectra as set by the delta-p parameter for the probabilistic KNN algorithm. The delta-p parameter may be increased up or down depending on the level of confidence desired to associate test spectra with the training set. In a blind test study, the delta-p parameter was set to 0.2 and a prediction result of 92% accuracy resulted.

While FIG. 11 is useful in graphically representing spectra in two-dimensional feature space, real world spectra typically result in 8-12 dimensional feature space, often reaching 8-12 dimensions or higher. Higher or lower dimensional feature space may be determined to be adequate or necessary in determining whether a cancer patient will be responsive to an anti-cancer drug. Thus, in certain embodiments a practitioner might utilize only one or two differential peaks, in other embodiments three or four differential peaks would be used, in still other embodiments five or six differential peaks would be used, in yet other embodiments seven or eight differential peaks would be used, in still yet other embodiments nine or ten differential peaks would be used and in other embodiments eleven or twelve differential peaks would be used. Indeed, adding even more differential peaks than twelve is contemplated by the invention. The determination of the number of features that provide enough information to be deterministic may be based on a number of factors, including amplitude of the features, classification of the spectra, and patient response to the anti-cancer treatment, for example.

Continuing with FIG. 3, a database, such as database 220 (FIG. 2), may be utilized to receive and store differentiating peaks, mass spectrometer diagnostics, and/or other output parameters from the classification and diagnostic process as described. These parameters may be stored and used for future classification of new spectra from new cancer patients. Eventually, the database may become populated to the extent that accuracy and reliability in classifying test spectra substantially ensure to a high probability, such as 98%, that a cancer patient will respond to the anti-cancer drug.

FIG. 12 is a Kaplan-Meyer plot 1200 of test data showing survival rates of groups of patients as classified in accordance with the principles of the present invention. The Kaplan-Meier plot 1200 is a mortality plot that indicates the survival rates over certain durations of time. As shown, those cancer patients who were categorized as "good" lived the longest due to receiving the anti-cancer drug. Those cancer patients who were categorized as "bad" had a steep drop-off in the first few months. Those cancer patients who were categorized as "undefined" steadily declined with a low survival rate. This plot was obtained in the discovery phase by testing a classifier trained on Italian 1 samples on Japanese 1 and 2 samples.

FIG. 13 is a Kaplan-Meier plot 1300 similar to FIG. 12 where a classifier trained on the Japanese samples 1 and 2 was tested on the Italian 1 set. As shown, patients whose associated spectrum were classified as "good" were predicted to have extended life from treatment with the anti-cancer drug. Patients classified as "bad" were predicted to have a steep mortality rate with a small percentage extending beyond a year. Those patients classified as 'undefined' had a steep decline and none were predicted to live beyond six months. These predictions proved to be accurate with the clinical tests.

FIG. 14 is a Kaplan-Meier plot 1400 similar to FIGS. 12 and 13 obtained from using the validated classifier blindly on the Italian 2 samples. At the time of the test, there was no knowledge of the survival data as it was maintained confidential. After the classification was performed, the survival data was disclosed, and the curves in FIG. 14 confirmed the results from the development testing. As shown, the patients classified as "good" were predicted to have an extended survival rate, and those classified as 'bad' had a steep drop-off with a more limited lifespan. In this particular case, the test was run with a low delta-p, so there were no patients classified as "undefined." Again, the results were consistent with the actual clinical test.

Figure 15:
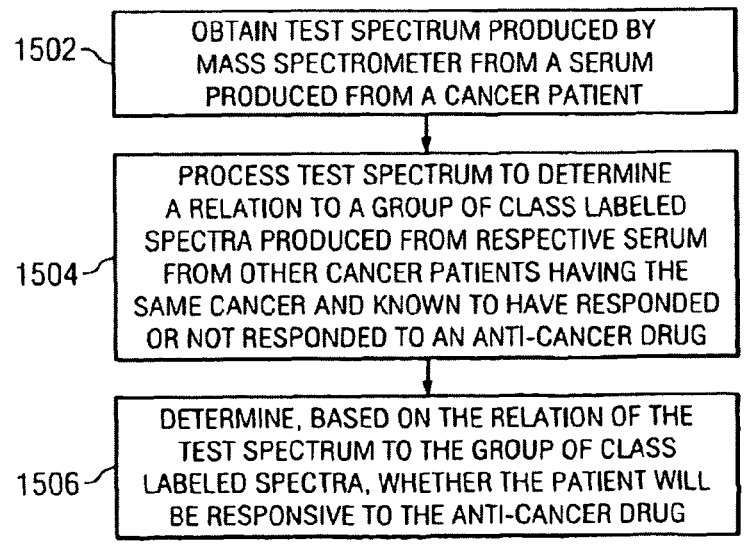
FIG. 15 is a block diagram of an exemplary process for determining whether a cancer patient will be responsive to an anti-cancer drug in accordance with the principles of the present invention.

FIG. 15 is a block diagram of an exemplary process 1500 for determining whether a cancer patient will be responsive to an anti-cancer drug in accordance with the principles of the present invention. The process 1500 starts at step 1502 where a test spectrum produced by a mass spectrometer from a serum produced from a cancer patient is obtained. At step 1504, the test spectrum is processed to determine a relation to a group of class labeled spectra produced from respective serum from other cancer patients having the same or similar clinical stage cancer and known to have responded or not responded to an anti-cancer drug. The relation means that the test spectrum is more likely to be associated or have the same or similar characteristics as one or another class labeled spectra. The anti-cancer drug may be one that treats non-small-cell lung cancer. At step 1506, a determination, based on the relation of the test spectrum to the group of classified spectrum, whether the patient will be responsive to the anti-cancer drug. Being responsive means that the anti-cancer drug will have some positive benefit for the cancer patient. The positive response will hopefully extend the patient's life, but other positive benefits may result from the cancer patient being treated with the anti-cancer drug.

The biomarkers measured by the instant invention may be any type of quantifiable parameters that appears as a peak in a mass spectroscopy spectrum. The parameter that causes the mass spectroscopy peak may be caused by any substance, including but not limited to, specific enzymes, hormones, mRNA, DNA, RNA, proteins, lipids, vitamins, minerals, metabolites, and chemical compounds. Further, the biomarkers can be measured from any tissue or fluid collected from the patient, including but not limited to, serum, red blood cells, white blood cells, nail, skin, hair, biopsied tissue, cerebral spinal fluid, bone marrow, urine, feces, sputum, bile, bronchoalveolar fluid, pleural fluid, and periotoneal fluid.

Biomarkers can reflect a variety of disease characteristics, including the level of exposure to an environmental or genetic trigger, an element of the disease process itself, an intermediate stage between exposure and disease onset, or an independent factor associated with the disease state, but not causative of pathogenesis. As such, it is contemplated that the principles of the present invention may also be applicable to determine specific stages of disease and disorders.

Although the examples of the principles of the present invention have been described with respect to Non-Small-Cell Lung Cancer and treatment with certain anti-cancer drugs, it should be understood that the principles may be applied to other cancers and other anti-cancer drugs available now or in the future. Further, the principles and methods of the present invention may be applied to detection of any disease or disorder, including not limited to cancer, autoimmune diseases or disorders, diabetes, genetic diseases or disorders, viral infections, bacterial infections, parasitic infections, prion diseases, nutritional deficiencies, vitamin deficiencies, mineral deficiencies, mitochondrial diseases or disorders, sexually transmitted diseases or disorders, birth defects, sexual diseases or disorders, immune diseases or disorders, balance diseases or disorders, pain, systemic diseases or disorders, blood diseases or disorders, blood vessel diseases or disorders, nerve diseases or disorders, musculature diseases or disorders, heart diseases or disorders, spinal diseases or disorders, eye diseases or disorders, mental diseases or disorders, metabolic diseases or disorders, internal organ diseases or disorders, lung diseases or disorders, liver diseases or disorders, kidney diseases or disorders, gall bladder diseases or disorders, pancreas diseases or disorders, gastrointestinal diseases or disorders, prostate diseases or disorders, gynecological diseases or disorders, and hearing diseases or disorders. Further, the principles and methods of the present invention may also be applied to determine if a treatment will work for environmental exposure and its effects, substance abuse, and epidemiological studies.

The principles and methods of the present invention may be applied to any drug treatment, including but not limited to general anesthetic drugs, anxiety and sleep disorder drugs, psychiatric disorder drugs, antipsychotic agents, affective disorder drugs, movement disorder drugs, epileptic and antiepileptic drugs, drugs to manage heart failure, anti-ischemic drugs, antiarrhythmic drugs, vascular drugs, cardiovascular and pulmonary drugs, opioid analgesics and antagonists, bronchodilators, anti-inflammatory drugs, drugs to manage bronchospastic disease, cromolyn sodium and related drugs, respiratory stimulants, antitussive drugs, drugs that modulate mucociliary transport, diuretics, antidiuretic hormones, synthetic analogues, and related drugs, insulin, glucagon, oral hypoglycemic agents, drugs to treat diabetes mellitus, parathyroid hormone drugs, bisphosphonates, calcitonin, adrenal corticosteroids, corticotropin releasing hormone, adrenocorticotropin, and antiadrenal drugs, thyroid hormones, thyroid stimulating hormone, thyrotropin releasing hormone, and antithryoid drugs, estrogens, antiestrogens, progestins, contraception, androgenic and anabolic and antagonists, gonadotropins, antiprogestins, activins, inhibins, gonadotropin-releasing hormone (GNRH), GNRH supragonists, and antagonists, growth hormone, insulin-like growth factors, prolactin, drugs to treat a thyperprolactinemic state, fat-soluble vitamins, water-soluble vitamins, macrominerals, -microminerals, fluorides, laxatives, antidiarrheal drugs, drugs affecting gastrointestinal motility, antiemetic agents, drugs that act on blood and blood-forming organs, drugs that act on the immune systems, nonopiate analgesics, anti-inflammatory drugs, plasma lipid modifying agents, topical corticosteroids, tars, dithranol, zinc preparations, retinoids, antimicrobial compounds, keratinization treatment drugs, drugs to treat ectoparasites, drugs to treat neoplastic disorders of skin, antihistamines, treatment of blistering disorders of the skin, sulfonamides, sulfones, trimethoprin-sulfamethoxazole, aminoglycosides, tetracyclines, chloramphenicol, erythromiycin, protein synthesis inhibitors, fluoroquinolones, quinolones, nitrofurans, methenamine, β-lactam antibiotics, drugs to treat mycobacterial infections, antifungal agents, antiviral drugs, antiparasitic drugs, and cancer chemotherapeutic drugs.

In addition, the principles of the present invention may be applicable to species other than human. While described as utilizing serum to perform the classification and analysis, it should be understood that various aspects of the principles of the present invention could similarly be applied by using other liquids or tissue samples to generate spectra capable of having differentiating peaks for determining if a cancer patient has characteristics of other cancer patients who responded to an anti-cancer drug.

The previous detailed description is of a small number of embodiments for implementing the invention is not intended to be limiting in scope. Once of skill in this art will immediately envisage the methods and variations used to implement this invention in other areas than those described in detail. The following claims set forth a number of the embodiments of the invention disclosed with greater particularity.

We claim:

1. A laboratory test processing center, comprising:
    one or more data storage devices storing (a) class-labeled mass spectral data obtained from blood-based samples of a multitude of cancer patients, the class labels for the mass spectral data indicating whether or not a patient associated with the mass spectral data responded to treatment of cancer from administration of an epidermal growth factor receptor pathway targeting drug; and (b) a mass spectrum of a blood-based sample of a cancer patient to be tested;
    a processing unit operating in accordance with a set of instructions to perform the following operations on the mass spectrum of the blood-based sample of a patient to be tested and the class-labeled mass spectral data:
        (a) perform one or more predefined pre-processing steps on the mass spectrum of the blood-based sample of a patient to be tested;
        (b) obtain integrated intensity values of features in the mass spectrum of the blood-based sample of a patient to be tested at one or more predetermined m/z ranges in said mass spectrum after the performance of said predefined pre-processing steps;
        (c) implement a classification algorithm on the integrated intensity values and the class-labeled mass spectral data, the classification algorithm assigning a class label for the blood-based sample of a patient to be tested indicating whether or not the said patient is likely to benefit from administration of an epidermal growth factor receptor pathway targeting drug; and
        (d) output the class label assigned by the classification algorithm to the blood-based sample of a cancer patient to be tested;
    wherein the cancer patient is a non-small cell lung cancer patient, and
    wherein the class label assigned to the blood-based sample of cancer patient to be tested indicates wherein the patient is likely to benefit from administration of at least one of (a) gefitinib and (b) erlotinib.

2. The laboratory test processing center of claim 1, further comprising a mass spectrometer, wherein the mass spectrometer produces a mass spectrum from a raw blood-based sample of the cancer patient and wherein the mass spectrum is stored in the one or more data storage devices.

3. The laboratory test processing center of claim 1, wherein the class-labeled spectra comprise class-labeled spectra from a multitude of non-small cell lung cancer patients.

4. The laboratory test processing center of claim 1, wherein the one or more predetermined m/z ranges are selected from the group of m/z ranges consisting of:
    5732 to 5795
    5811 to 5875
    6398 to 6469
    11376 to 11515
    11459 to 11599
    11614 to 11756
    11687 to 11831
    11830 to 11976
    12375 to 12529
    23183 to 23525
    23279 to 23622
    65902 to 67502.

5. The laboratory test processing center of claim 1, wherein the classification algorithm comprises a k-nearest neighbor classification algorithm.

6. The laboratory test processing center of claim 5, wherein the classification algorithm comprises a probabilistic k-nearest neighbor classification algorithm.

7. The laboratory test processing center of claim 1, wherein the predefined pre-processing steps comprise:
    a) subtracting background contained in the mass spectrum of the blood-based sample of the patient to be tested to produce a background subtracted spectrum, wherein the subtracting step comprises estimating non-constant levels of background and subtracting the estimated background from the mass spectral data;
    b) normalizing the background subtracted spectrum; and
    c) aligning the normalized, background subtracted spectrum to a predefined mass scale.

8. The laboratory test processing center of claim 7, wherein the subtracting background step estimates non-constant levels of background in a moving window comprising a range of m/z values in said mass spectral data using robust asymmetric estimates of background.

* * * * *